(12) United States Patent
Behar

(10) Patent No.: US 8,870,772 B2
(45) Date of Patent: **\*Oct. 28, 2014**

(54) METHOD AND SYSTEM FOR TISSUE RECOGNITION

(75) Inventor: Boaz Behar, Ganei Tikva (IL)

(73) Assignee: Perseus-BioMed Inc., Orangeburg, NY (US)

( * ) Notice: Subject to any disclaimer, the term of this patent is extended or adjusted under 35 U.S.C. 154(b) by 277 days.

This patent is subject to a terminal disclaimer.

(21) Appl. No.: 12/648,433

(22) Filed: Dec. 29, 2009

(65) Prior Publication Data

US 2011/0087096 A1 Apr. 14, 2011

Related U.S. Application Data

(60) Provisional application No. 61/182,781, filed on Jun. 1, 2009, provisional application No. 61/193,815, filed on Dec. 29, 2008.

(51) Int. Cl.
*A61B 8/00* (2006.01)
*A61B 8/12* (2006.01)
*A61B 5/01* (2006.01)
*A61B 10/02* (2006.01)
*A61B 8/08* (2006.01)

(52) U.S. Cl.
CPC ............ *A61B 5/01* (2013.01); *A61B 10/0233* (2013.01); *A61B 8/0841* (2013.01); *A61B 8/12* (2013.01); *A61B 8/085* (2013.01); *A61B 8/48* (2013.01)
USPC ........................................................ 600/438

(58) Field of Classification Search
CPC .................. A61B 5/01; A61B 8/085
USPC ........................................................ 600/438
See application file for complete search history.

(56) References Cited

U.S. PATENT DOCUMENTS

| | | | |
|---|---|---|---|
| 4,059,010 A | 11/1977 | Sachs | |
| 4,428,382 A * | 1/1984 | Walsall et al. | 600/549 |
| 4,621,929 A | 11/1986 | Phillips | |
| 4,807,633 A * | 2/1989 | Fry | 600/438 |
| 4,995,398 A | 2/1991 | Turnidge | |
| 5,935,075 A | 8/1999 | Casscells et al. | |

(Continued)

FOREIGN PATENT DOCUMENTS

| | | |
|---|---|---|
| JP | 2008-509777 | 4/2008 |
| WO | WO 03/096883 | 11/2003 |

(Continued)

OTHER PUBLICATIONS

Bounaïm et al. "Sensitivity of the Ultrasonic CARI Technique for Breast Tumor Detection Using A FETD Scheme", Ultrasonics, 42: 919-925, 2004.

(Continued)

*Primary Examiner* — Jonathan Cwern

(57) ABSTRACT

A method for characterizing body tissue, comprising:
a) transmitting ultrasound into tissue of a body, heating the body tissue by less than 3 degrees Celsius;
b) measuring temperature of the tissue, at one or more locations at one or more times during the ultrasound transmission, following the ultrasound transmission, or both; and
c) using the temperature measurement to determine at least one property of the body tissue, based on differences in absorption of ultrasound, differences in cooling rate of the tissue following the ultrasound transmission, or both.

34 Claims, 9 Drawing Sheets

(56) References Cited

U.S. PATENT DOCUMENTS

| | | | |
|---|---|---|---|
| 6,728,567 | B2 | 4/2004 | Rather et al. |
| 7,211,044 | B2 | 5/2007 | Mast et al. |
| 2002/0128570 | A1* | 9/2002 | Bowman et al. ............. 600/567 |
| 2003/0171691 | A1 | 9/2003 | Casscells, III et al. |
| 2004/0030227 | A1 | 2/2004 | Littrup et al. |
| 2004/0102722 | A1 | 5/2004 | Naghavi |
| 2004/0236225 | A1 | 11/2004 | Murphy et al. |
| 2007/0106157 | A1 | 5/2007 | Kaczkowski et al. |
| 2007/0213617 | A1 | 9/2007 | Berman et al. |
| 2008/0081995 | A1 | 4/2008 | Kim et al. |
| 2008/0119729 | A1* | 5/2008 | Copa et al. .................... 600/435 |
| 2008/0200795 | A1 | 8/2008 | Steckner |
| 2008/0319355 | A1* | 12/2008 | Nita ................................. 601/2 |
| 2009/0105588 | A1 | 4/2009 | Emelianov et al. |
| 2009/0287082 | A1 | 11/2009 | Lizzi et al. |
| 2012/0316439 | A1 | 12/2012 | Behar |

FOREIGN PATENT DOCUMENTS

| | | |
|---|---|---|
| WO | WO 2004/016177 | 2/2004 |
| WO | WO 2006/018837 | 2/2006 |
| WO | WO 2008/038182 | 4/2008 |
| WO | WO 2008/067079 | 6/2008 |
| WO | WO 2009/083973 | 7/2009 |

OTHER PUBLICATIONS

Despotović et al. "Using Phase Information in Ultrasound RF-Signals for Tissue Characterization", ProRISC, Nov. 2008, p. 314-317.
Severcan et al. "Ultrasound Propagation Through Biological Tissues", Studia Universitatis BabeBabeş -Bolyai, Physica, Special Issue, 7 P., 2001.
Van Venrooij "Measurement of Ultrasound Velocity in Human Tissue", Ultrasonics, p. 240-242, Oct. 1971.
Arthur et al. "Change in Ultrasonic Backscattered Energy for Temperature Imaging: Factors Affecting Temperature Accuracy and Spatial Resolution in 3D", 32nd UITC, 2005, 20 pages.
Curiel et al. "HIFU and Chemotherapy Synergistic Inhibitory Effect on Dunning AT2 Tumour-Bearing Rats", 4th International Symposium on Therapeutic Ultrasound, AIP Conference Proceedings, 754: 191-195, Mar. 28, 2005.
Dong et al. "In Vivo Measurements of Frequency-Dependent Attenuation in Tumors of the Liver", Journal of Clinical Ultrasound (JCU), 22(3): 167-174, Mar.-Apr. 1994. Abstract.
EDAP TMS "EDAP Announces Launch of Clinical Study Combining HIFU and Chemotherapy for Localized Aggressive High Risk Prostate Cancer", Bio-Medicine, 3 P., Aug. 19, 2007.
Farnoud et al. "Ultrasound Backscatter Signal Characterization and Classification Using Autoregressive Modeling and Machine Learning Algorithms", Proceedings of the 25h Annual International Conference of the IEEE EMBS Cancun, Mexico, Sep. 2003, p. 2861-2864.
Gleiter et al. "Ultrasound—Lockin-Thermography for Advanced Depth Resolved Defect Selective Imaging", ECNDT, We.3.8.2, p. 1-7, 2006.
Hollis "Non-Invasive Monitoring of Brain Tissue Temperature by Near-Infrared Spectoscopy", Thesis Submitted for the Degree of Ph.D. at the University of London, 2002, 18 pages. Abstract, acknowledgments, contents, chapter 4.
Kolios et al. "Spatial Correlation of Flow Induced Temperature Gradients During Tissue Heating with Vascular Geometry Using CT Angiography: Implications for Thermal Therapy", Physics Publications and Research, Paper 29, 1997, 3 pages.
Liu et al. "Ultrasonic Characterization of Porcine Liver Tissue at Frequency Between 25 to 55 MHz", World Journal of Gastroenterology, 12(14): 2276-2279, Apr. 14, 2006.
Phillips et al. "Guidance for Industry and FDA Staff. Information for Manufacturers Seeking Marketing Clearance of Diagnostic Ultrasound Systems and Transducers", Sep. 9, 2008, 68 pages.
Phillips et al. "Information for Manufacturers Seeking Marketing Clearance of Diagnostic Ultrasound Systems and Transducers", Guidance for Industry and FDA Staff, US Department for Food and Drug Administration, p. i-iv, 1-64, Sep. 9, 2008.
Seip et al. "Noninvasive Estimation of Tissue Temperature Response to Heating Fields Using Diagnostic Ultrasound", IEEE Transactions on Biomedical Engineering, 42(8): 828-839, 1995.
Seip et al. "Real-Time Detection of Multiple Lesions During High Intensity Focused Ultrasound (HIFU) Treatments", International Symposium on Therapeutic Ultrasound, Seattle, USA, 8 P. 2002.
Severcan et al. "Ultrasound Propagation Through Biological Tissues", Studia Universitatis BabeBabeş -Bolyai, Physica, Special Issue, 7 P., 2001.
Sfez et al. "Electro-Optical Ultrasound", IAEC, Annual Report, p. 1-23, 2001.
International Search Report and the Written Opinion Dated May 23, 2011 From the International Searching Authority Re. Application No. PCT/IB2010/056117.
O'Brien Jr. "Ultrasound-Biophysics Mechanisms", Progress in Biophysics and Molecular Biology, XP005781585, 93(1-3): 212-255, Nov. 28, 2006. Abstract, p. 235, § 2, Fig.10.
O'Brien Jr. et al. "Evaluation of the Unscanned Soft-Tissue Thermal Index", IEEE Transactions on Ultrasonics, Ferroelectrics and Frequency Control, XP011090152, 46(6): 1459-1476, Nov. 1, 1999.
Stoner et al. "Relationship Between Blood Velocity and Conduit Artery Diameter and the Effect of Smoking on Vascular Responsiveness", Journal of Applied Physiology, 96: 2139-2145, Jun. 2004.
Official Action Dated May 4, 2012 From the US Patent and Trademark Office Re. U.S. Appl. No. 12/648,440.
International Preliminary Report on Patentability Dated Jul. 12, 2012 From the International Bureau of WIPO Re. Application No. PCT/IB2010/056116.
International Search Report and the Written Opinion Dated May 26, 2011 From the International Searching Authority Re. Application No. PCT/IB2010/056116.
Despotovic et al. "Using Phase Information in Ultrasound RF-Signals for Tissue Characterization", ProRISC, Nov. 2008, p. 314-317.
Landini et al. "Evaluation of the Attenuation Coefficients in Normal and Pathological Breast Tissue", Medical & Biological Engineering & Computing, 24(3): 243-247, May 1986. Abstract. http://www.springerlink.com/content/h6k25v1314720870.
O'Brien Jr. et al. "Evaluation of the Unscanned Soft-Tissue Thermal Index", IEEE Transactions on Ultrasonics, Ferroelectrics and Frequency Control, XP011090152, 46(6): 1459-1476, Nov. 1, 1999. Abstract.
Official Action Dated Nov. 16, 2012 From the US Patent and Trademark Office Re. U.S. Appl. No. 12/648,440.
Rantala et al. "Lock-In Thermography With Mechanical Loss Angle Heating at Ultrasonic Frequencies", Proceedings of the Eurotherm Seminar, 50: 389-393, Sep. 1996.
Straube et al. "An In Vivo System for the Determination of the Effect of Temperature on Backscattered Ultrasound Energy in Ultrasonic Images", Society for Thermal Medicine, Bethesda, Maryland, Apr. 1-3, 2005.
Zweschper et al. "Ultrasound Excited Thermography Using Frequency Modulated Elastics Waves", Proc. SPIE 5073, Thermosense XXV, 386, 7 P, Apr. 3, 2003.
Official Action Dated Jul. 30, 2013 From the US Patent and Trademark Office Re. U.S. Appl. No. 12/648,440.
Advisory Action Before the Filing of an Appeal Brief Dated Jan. 8, 2014 From the US Patent and Trademark Office Re. U.S. Appl. No. 12/648,440.
Applicant-Initiated Interview Summary Dated Nov. 14, 2013 From the US Patent and Trademark Office Re. U.S. Appl. No. 12/648,440.
Notice of Allowance Dated Aug. 14, 2014 From Re. U.S. Appl. No. 13/519,604.
Notice of Allowance Dated Aug. 15, 2014 From the Re. U.S. Appl. No. 12/648,440.
Notice of Reason for Rejection Dated Jul. 29, 2014 From the Japanese Patent Office Re. Application No. 2012-546549 and Its Translation Into English.

* cited by examiner

METHOD AND SYSTEM FOR TISSUE RECOGNITION

RELATED APPLICATIONS

This application claims the benefit under 35 U.S.C. §119 (e) from U.S. Provisional Patent Application Nos. 61/182,781 filed on Jun. 1, 2009, and 61/193,815 filed on Dec. 29, 2008.

The contents of all of the above documents are incorporated by reference as if fully set forth herein.

FIELD AND BACKGROUND OF THE INVENTION

The present invention, in some embodiments thereof, relates to a system that determines at least one property of a body tissue by its thermal response during and/or following exposure to ultrasound, and, more particularly, but not exclusively, to a system that distinguishes cancerous from normal tissue using such methods.

A number of medical imaging modalities are used for distinguishing different types of body tissue, and in particular for locating cancer and other diseased tissue, but each of these modalities has some disadvantages. Ultrasound imaging does not distinguish well between some types of soft tissue. X-rays, especially if used for computerized tomography (CT) scans, can distinguish some types of soft tissue, but the resolution and noise level of x-ray images is limited by the harmful effects of too much radiation, and this is especially true of CT images which require much higher x-ray doses than ordinary x-ray images. Magnetic resonance imaging (MRI) is typically better than ultrasound at distinguishing soft tissues, but MRI equipment is generally large and expensive, and often surrounds the patient, providing limited access for performing other procedures in real time. CT equipment, and equipment for nuclear medicine imaging, such as PET, also tends to be large and expensive. Infrared imaging can locate regions on the surface of the body that differ in temperature from surrounding regions, but has limited utility for finding diseased tissue, since the body's temperature control mechanisms tend to make the temperature uniform.

Biopsies are also used for identifying cancer and other diseases, but biopsies are invasive, carrying a risk of infection, and are often uncomfortable for the patient. Furthermore, if a biopsy is done without knowing the location of the suspected diseased tissue, as is normally the case with prostate biopsies, then it may miss the diseased tissue, giving a false negative result.

Ultrasound is used medically both for imaging and for therapy. Ultrasound medical imaging systems generally use short pulses of ultrasound, between 200 and 5000 pulses per second. Safety regulations, for example by the United States Food and Drug Administration (FDA) generally limit ultrasound imaging systems to relatively low time average power, which do not cause the temperature the exposed tissue to increase by more than 3 degrees Celsius. The power within each pulse is generally much greater than average power, to provide adequate signal to noise ratio. For example, FDA regulations limit spatial peak time average power to 720 mW/cm$^2$, but spatial peak pulse average power can be as high as 190 W/cm$^2$. As used herein, "spatial peak time average power" and "spatial peak pulse average power" both refer to the global maximum derated power, as defined in "Information for Manufacturers Seeking Marketing Clearance of Diagnostic Ultrasound Systems and Transducers," FDA Document 560, issued Sep. 9, 2008.

Ultrasound therapy systems use higher power, and generally increase the temperature of treated tissue by more than 3 degrees Celsius. Some ultrasound therapy systems heat tissue to a much higher temperature over a small volume, in order to ablate it. Ralf Seip et al, "Real-Time Detection of Multiple Lesions During High Intensity Focused Ultrasound (HIFU) Treatments," presented at *International Symposium on Therapeutic Ultrasound*, Seattle, 2002, describes an ultrasound therapy system that produces lesions by locally heating tissue to more than 85 degrees C. using 30 to 37 watts total acoustic power, in which the lesions are monitored in real time using scattered ultrasound.

U.S. Pat. No. 7,211,044 to Mast et al describes a therapeutic ultrasound system, in which a low intensity ultrasound signal is first focused on a target tissue, producing a temperature rise of less than 1 degree C. The temperature rise in the target tissue is imaged, to ensure that the ultrasound signal was correctly aimed at the target tissue, and high intensity ultrasound is then focused on the target tissue to administer hyperthermia treatment or to ablate the tissue.

G. E. P. M. Van Venrooij, "Measurement of ultrasound velocity in human tissue," Ultrasonics, October 1971, p. 240-242, gives data on the sound speed and acoustic impedance for ultrasound in blood, cerebrospinal fluid, and different types of brain tumors. Ferride Severcan, Dana Dorohoi, and Dorina Creanga, "Ultrasound Propagation Through Biological Tissues," Studia Universitatis Babes-Bolyai, Physica, Special Issue, 2001, p. 169-175, gives the sound speed, acoustic impedance, and absorption coefficient for ultrasound at different frequencies and temperatures in different types of body tissue, and suggests that information about the presence of tumors or foreign bodies can be obtained using physical parameters characterizing ultrasound propagation in tissues.

The online newsletter Bio-Medicine, in an article dated Aug. 17, 2007 and downloaded from <http://www.bio-medicine.org/medicine-technology-1/EDAP-Announces-Launch-of-Clinical-Study-Combining-HIFU-and-Chemotherapy-for-Localized-Aggressive-High-Risk-Prostate-Cancer-4-1/> on Mar. 24, 2009, describes a clinical trial by EDAP TMS S.A. in Lyon, France, a global leader in High Intensity Focused Ultrasound (HIFU) treatment of prostate cancer, in which therapeutic ultrasound is used to ablate stage T2c prostate cancer, in conjunction with chemotherapy agents. The efficacy of the chemotherapy agent in the surrounding tissue is said to be improved by the ultrasound treatment. A synergistic effect of combining ultrasound treatment with chemotherapy in an animal study is reported by Curiel et al, "HIFU and Chemotherapy Synergistic Inhibitory Effect on Dunning AT2 Tumour-Bearing Rats," *4$^{th}$ International Symposium on Therapeutic Ultrasound*, AIP Conference Proceedings, Volume 754, pp. 191-195 (2005).

A. Bounaim et al, "Sensitivity of the ultrasonic CARI technique for breast tumor detection using a FETD scheme," Ultrasonics 42, 919-925 (2004) describes a simulation of the CARI (clinical amplitude/velocity reconstruction imaging) technique for ultrasound detection of breast cancer, which is said to have "demonstrated clinical potential for improving the differentiation of benign and malignant breast lesions." The paper cites "clinical studies of the CARI modality [which] have shown that the sound velocity and the acoustic tissue attenuation are important quantitative parameters in characterizing the different tissues of the female breast."

Bao-wei Dong et al, "In vivo measurements of frequency-dependent attenuation in tumors of the liver," Journal of Clinical Ultrasound 22, 167-174 (1994), describes measurements of the frequency dependence of ultrasound attenuation in the livers of healthy subjects and subjects with different types of benign and malignant liver tumors. Some of the types of tumors showed higher frequency dependence of attenuation than healthy tissue, while other types of tumors showed lower frequency dependence of attenuation than healthy tissue.

Xiao-Zhou Liu et al, "Ultrasonic characterization of porcine liver tissue at frequency between 25 to 55 MHz," World J Gastroenterol Apr. 14, 2006; 12(14): 2276-2279, describes greater attenuation of ultrasound found in cirrhotic porcine liver tissue than in normal porcine liver tissue.

L. Landini et al, Medical and Biological Engineering and Computing 24, 243-247 (1986), "reports on measurements of frequency-dependent attenuation of ultrasound in normal and pathological breast tissue . . . including fatty tissue, fibrofatty parenchyma and fibrosis, and malignant tumors with and without productive fibrosis (infiltrating ductal carcinoma scirrhous type and medullary carcinoma, respectively) . . . . The results of the attenuation measurements indicate that the attenuation coefficient is lower for tissues with large predominance of cells (fatty tissue, medullary carcinoma) and increases with collagen fiber content (infiltrating ductal carcinoma scirrhous type, fibrosis, fibrofatty)."

B. Sfez et al, "Electro-Optical Ultrasound," Israel Atomic Energy Commission Annual Report, 2001, p. 1-23, downloaded from <http://www.iaec.gov.il/docs/IAEC20.pdf> on Feb. 24, 2009, describes a medical imaging method in which visible or infrared light is transmitted into tissue, and focused ultrasound waves are used to scan the tissue. Although the light is strongly diffused by the tissue, the part of the light that passed through the location where the ultrasound is focused can be identified by its modulation at the ultrasound frequency, and in this way a 3-D map can be reconstructed of the absorption of the light in the tissue.

Victoria S. Hollis, "Non-Invasive Monitoring of Brain Tissue Temperature by Near-Infrared Spectroscopy," Ph.D. thesis, Dept. of Medical Physics and Bioengineering, University of London, September 2002, in Chapter 4, reviews various methods of measuring brain temperature non-invasively, including near-infrared spectroscopy (NIRS), microwave radiometry, magnetic resonance thermometry, and ultrasound thermometry.

The use of ultrasound to measure tissue temperature non-invasively is also described by W. L. Straube, J. Parry, E. Moros, J. Trobaugh, and R. M. Arthur, in a talk "An In Vivo System for the Determination of the Effect of Temperature on Backscattered Ultrasound Energy in Ultrasonic Images," presented at 2005 Annual Meeting, Society for Thermal Medicine, Bethesda, Md., Apr. 1-3, 2005, and by R. M. Arthur et al, in a talk "Change in Ultrasonic Backscattered Energy for Temperature Imaging Factors Affecting Temperature Accuracy and Spatial Resolution in 3-D," presented at the $32^{nd}$ UITC, Alexandria, Va., May 16, 2007. The authors consider ultrasound backscattering from an inhomogeneous tissue, such as liver tissue with small inclusions of aqueous and lipid material, which have ultrasound backscattering coefficients that have different dependence on temperature. They describe using the resulting spatial variation in backscattering energy to measure the temperature of the tissue.

Seip and Ebbini, "Noninvasive Estimation of Tissue Temperature Response to Heating Fields Using Diagnostic Ultrasound," IEEE Transactions on Biomedical Engineering, vol 42, pp. 828-839 (1995), describe another technique for using backscattering of diagnostic ultrasound to monitor temperature changes in tissue. The technique is based on the observation that most biological tissues are semi-regular scattering lattices. These lattice structures produce harmonics in the backscattered ultrasound, with the frequency shift of the harmonics depending on temperature, through the temperature dependence of the sound speed, and the thermal expansion of the lattice structure. Autoregressive model-based methods are used to estimate the frequency shift.

Ultrasound has been used for non-destructive testing of a variety of materials, including ceramics, metals, and plastics. Cracks and other defects inside the material may absorb ultrasound more than the bulk material, and are detected by the increased temperature they produce at the surface of the material, which is measured. Typically, the ultrasound transducers produce power densities of more than 100 W/cm$^2$, and are modulated at frequencies ranging from a few Hz down to a few hundredths of a Hz. Examples of such systems are described in Th. Zweschper et al, "Ultrasound excited thermography using frequency modulated elastic waves," in "Insight," ISSN 1354-2575, 2003, vol. 45, #3, pp 178-182 (British Institute of Nondestructive Testing); J. Rantala et al, "Lock-in thermography with mechanical loss angle heating at ultrasonic frequencies," *Quantitative Infrared Thermography*, Eurotherm Series 50, Edition ETS 1997, pp 389-393; and A. Gleiter et al, "Ultrasound-Lockin-Thermography for Advanced Depth Resolved Defect Selective Imaging," European Conference on Non-Destructive Testing 2006, paper We.3.8.2, downloaded from <http://www.ndt.net/article/ecndt2006/papers~1.htm> on Jan. 25, 2009.

SUMMARY OF THE INVENTION

An aspect of some embodiments of the invention concerns using ultrasound, at the relatively low power levels typically used for diagnostic ultrasound, to determine at least one property of a body tissue by its energy absorption and cooling properties.

There is thus provided, in accordance with an exemplary embodiment of the invention, a method for characterizing body tissue, comprising:
 a) transmitting ultrasound into tissue of a body, heating the body tissue by less than 3 degrees Celsius;
 b) measuring temperature of the tissue, at one or more locations at one or more times during the ultrasound transmission, following the ultrasound transmission, or both; and
 c) using the temperature measurement to determine at least one property of the body tissue, based on differences in absorption of ultrasound, differences in cooling rate of the tissue following the ultrasound transmission, or both.

Optionally, the ultrasound is transmitted into the body tissue at a spatial peak power level, time-averaged over any one second interval, of less than 720 mW/cm$^2$.

Optionally, determining at least one property of the body tissue comprises finding cancerous tissue and distinguishing it from normal tissue.

Optionally, the method also includes placing at least one brachytherapy seed at a location responsive to the location of the cancerous tissue.

Optionally, the cancerous tissue is distinguished by its greater heating rate by the ultrasound.

Additionally or alternatively, the cancerous tissue is distinguished by its more rapid cooling rate following the transmission of the ultrasound.

In an embodiment of the invention, measuring the temperature comprises measuring an emitted infrared distribution on an outer surface of the body.

Optionally, transmitting ultrasound comprises transmitting ultrasound at two different times, at two different frequencies that have different penetration depths in the tissue, measuring the temperature comprises measuring the emitted infrared distribution due to heating at each of the frequencies, and determining at least one property of the body tissue comprises determining dependence of the property on depth into the tissue.

Optionally, the tissue is breast tissue, and characterizing body tissue comprises locating breast cancer.

Optionally, using the temperature measurement comprises using image processing software to sharpen the measured infrared distribution.

In an embodiment of the invention, the method also includes placing an invasive probe in the tissue, wherein measuring the temperature is done along a path of the probe.

Optionally, the invasive probe comprises a biopsy needle or a needle for implanting brachytherapy seeds.

Optionally, the method also includes placing a biopsy needle in the tissue along a different path responsive to the location of the cancerous tissue, and taking a biopsy sample with the biopsy needle along the different path.

Optionally, the probe comprises a biopsy needle, and measuring the temperature is done by a moveable temperature sensor located inside the needle, also including removing the temperature sensor from the needle after measuring the temperature, to make room for a biopsy sample.

Optionally, the method also includes taking a biopsy sample with the needle, after measuring the temperature, at a location chosen in response to the location of the cancerous tissue as determined from said temperature measurement.

Optionally, the temperature is measured at a plurality of locations while the probe is in place, or sequentially as the probe is moved.

Optionally, the tissue comprises prostate tissue.

Optionally, measuring temperature of the tissue comprises using one or more of near infrared spectroscopy, microwave radiometry, ultrasound thermometry, magnetic resonance thermometry, and electric impedance tomography.

In an embodiment of the invention, transmitting the ultrasound is done continuously for an interval of at least 0.1 seconds.

There is further provided, in accordance with an exemplary embodiment of the invention, a system for characterizing of body tissue, comprising:
  a) an ultrasound transmitting system for transmitting ultrasound waves into the body tissue, limited to transmitting no more than 720 mW/cm$^2$ spatial peak power time-averaged over any one second interval; and
  b) a temperature measuring system that measures temperature of the body tissue at one or more locations during and/or following the transmission of the ultrasound waves into the tissues, thereby providing information for characterizing the tissue.

Optionally, the temperature measuring system comprises an infrared camera for measuring temperature on an outside surface of the body.

Optionally, the system also comprises a compressing element for compressing a breast, and the infrared camera is positioned for making a map of temperature over a surface of the compressed breast.

Optionally, the ultrasound transmitter is positioned for transmitting the ultrasound waves through the compressed breast over an extended area.

Optionally, the system also includes a biopsy needle or a needle for implanting brachytherapy seeds, and the temperature measuring system comprises at least one temperature sensor associated with the needle.

Optionally, the at least one temperature sensor comprises a plurality of temperature sensors arranged along the needle.

Additionally or alternatively, the at least one temperature sensor comprises a temperature sensor located inside the needle.

Optionally, the temperature mapping system is capable of measuring temperature with a precision of better than 0.5 degrees Celsius, with a spatial resolution of better than 1 cm, in an acquisition time of less than one minute.

Optionally, the system also includes a controller which determines at least one property of the body tissue using the temperature measurements.

Optionally, the controller takes into account a relative timing of the ultrasound transmitting and the temperature measuring in determining the property of the body tissue.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

The present invention, in some embodiments thereof, relates to a system that determines at least one property of a body tissue by its thermal response during and/or following exposure to ultrasound, and, more particularly, but not exclusively, to a system that distinguishes cancerous from normal tissue using such methods.

An aspect of some embodiments of the invention concerns a system for determining at least one property of a body tissue by transmitting ultrasound into the tissue at a spatial peak time-averaged power level no greater than 720 mW/cm$^2$, which is the United States FDA limit for diagnostic ultrasound, and measuring a temperature of the tissue at one or more locations during and/or following ultrasound transmission. Optionally, such a method is used to distinguish cancer or other disease states from normal tissue, since some types of cancer, for example, may absorb ultrasound more than normal tissue, heating up more, and may cool more rapidly than normal tissue following the ultrasound transmission, due to increased blood flow. Other types of cancer, or other diseased tissue, may instead absorb ultrasound less than normal tissue, heating up less. The method can also be used to determine the type of tissue at a given location.

Optionally, the temperature is measured on the outside of the body, using an infrared camera or scanner. This may be particularly useful, for example, for detecting breast cancer, especially if the breast is compressed so that any cancer will be close to the surface. Optionally, an infrared image of the surface of the body is sharpened, using image processing software, to better detect and locate a type of tissue, such as breast cancer, that is beneath the surface.

In an exemplary embodiment of the invention, the temperature in the tissue is measured internally, with an invasive probe that penetrates the tissue, for example a biopsy needle or brachytherapy needle in the prostate, using an array of temperature sensors arranged along the probe, or a single sensor near the end of the probe which optionally measures the temperature at different positions sequentially as the probe is moved. Optionally, the temperature measurements are used in choosing a location from which a biopsy sample is taken, or in choosing a location at which a brachytherapy seed is implanted.

Optionally, the ultrasound raises the temperature of the tissue by no more than 3 degrees Celsius. Optionally, ultrasound is transmitted continuously, or over intervals of at least 0.1 second without interruption.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Biopsy System

Figure 1A:
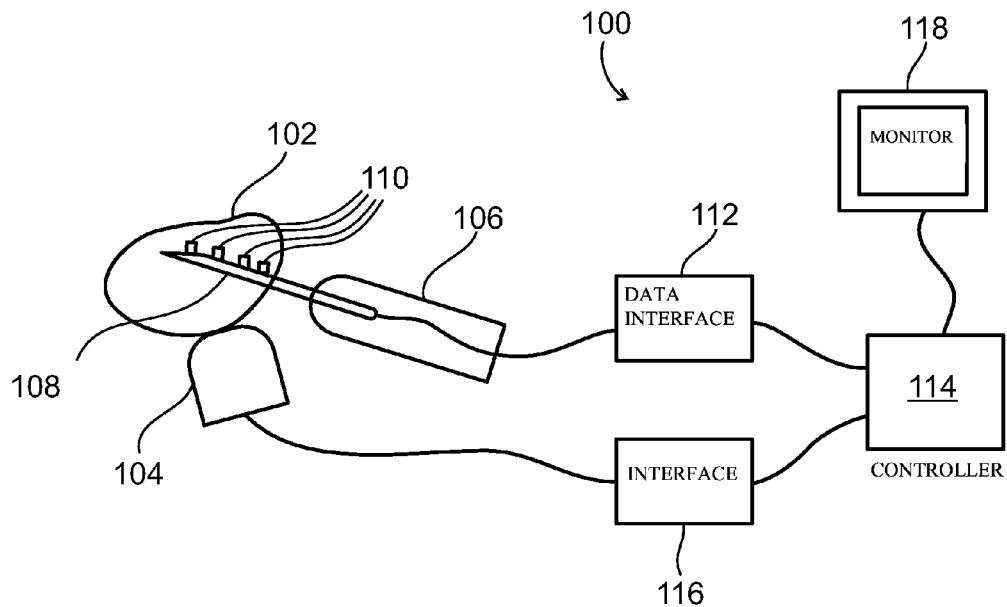
FIG. 1A is a schematic view of an ultrasound biopsy or brachytherapy system for the prostate, according to an exemplary embodiment of the invention.

Referring now to the drawings, FIG. 1A schematically illustrates a prostate biopsy system 100 according to an exemplary embodiment of the invention. System 100 makes ultrasound images of an organ of the body, for example a prostate gland 102, in real time, using an ultrasound transducer 104, for example a transrectal ultrasound transducer in the case of a prostate biopsy, or an array of such transducers, in order to guide a biopsy gun 106, when it advances biopsy needles 108 into the organ being biopsied. Optionally, transducer 104 also receives ultrasound scattered by the organ and other parts of the body, to provide the ultrasound images. Alternatively or additionally, one or more other ultrasound transducers serve as receivers for imaging.

The biopsy system will be described here in reference to the prostate, but such as system can be used as well for other parts of the body. In system 100, ultrasound transducer 104 transmits enough power into prostate 102 so that the temperature of the tissue increases measurably, due to absorption of some of the ultrasound power, even if that much power is not required for imaging. Malignant tumors in the prostate may tend to absorb heat at a different rate than the surrounding normal tissue, and heat up more rapidly or less rapidly than normal tissue, as suggested by the papers cited above which find different rates of ultrasound attenuation, and frequency dependence of attenuation, in normal and pathological breast and liver tissue.

Transducer 104 transmits ultrasound, for example, at a spatial peak time averaged power slightly less than 720 mW/cm$^2$, for example 700 mW/cm$^2$, or 500 mW/cm$^2$, or 400 mW/cm$^2$, or 300 mW/cm$^2$, or 200 mW/cm$^2$, or at intermediate values, or less than 200 mW/cm$^2$. The power is optionally distributed fairly uniformly over the dimensions of the transducer head, which is, for example, at least approximately square in shape, and 6 cm across, or 5 cm across, or 4 cm across, or 3 cm across, or a larger, smaller, or intermediate value. Optionally, the transducer is a standard size for a rectal ultrasound probe used for prostate imaging or therapy. In vitro tests by the inventor have found that dead tissue can be heated by 3 to 6 degrees Celsius in 2 to 4 minutes, using 700 mW/cm$^2$ of ultrasound power, distributed uniformly over a square 5 cm across, at a frequency of 1 MHz, and it is anticipated that the temperature rise in living tissue at this power level and frequency will be less, due to the thermal regulatory mechanisms of the body.

Optionally, the ultrasound power is distributed relatively uniformly throughout most of the prostate, so that differences in heating are due substantially to differences in absorption rate in the tissue, rather than being due almost entirely due to non-uniform ultrasound power distribution. In addition, if the tissue absorbs a significant fraction of the incident ultrasound power over a distance that is comparable to the dimensions of the prostate, and certain malignant tumors absorb more ultrasound than normal tissue, then these malignant tumors may be distinguished from normal tissue by having a greater temperature gradient. This may be expected to occur because those parts of the prostate that are in the "shadow" of a tumor which absorbs more ultrasound than the surrounding tissue would tend to be cooler. Conversely, if a malignant tumor is of a type that absorbs less ultrasound than normal tissue, then it may have a lower temperature gradient than nearby normal tissue.

One or more temperature sensors 110, for example thermocouples, are located on needle 108, and measure the temperature of the prostate along the path of needle 108. In some embodiments of the invention, a plurality of temperature sensors 110, arranged along the length of needle 108 as shown in FIG. 1A, measure temperature simultaneously when the needle is in place in the prostate. In some embodiments of the invention, there may be only one temperature sensor, for example at the tip of needle 108, and the temperature at different locations along the path of the needle is measured sequentially as the needle is withdrawn. Even if there is more than one temperature sensor, optionally the temperature at one or more intermediate positions is measured when the needle is withdrawn somewhat. In those cases where the temperature is measured as the needle is withdrawn, the needle is optionally withdrawn slowly enough, or pausing long enough at certain positions, so that the temperature sensor can equilibrate with its surroundings and accurately measure the temperature. Alternatively the needle is withdrawn more rapidly, but the finite equilibration time of the temperature sensor is taken into account in analyzing the results. The equilibration time of the temperature sensors is optionally determined experimentally in vitro, or calculated using a model that includes specific heat and thermal conductivity.

In some embodiments of the invention, at least one temperature sensor comprises a thermocouple built into the needle, optionally incorporating the wall of the needle as one of the metals of the thermocouple. Some of these embodiments of the invention will be described in more detail below, in the description of FIG. 10.

In some embodiments of the invention, one or more temperature sensors are located on or adjacent to the ultrasound transmitter, instead of or in addition to being located on the biopsy needle, and these sensors measure temperature at one or more locations adjacent to the outer surface of the prostate, for example at the rectal wall. Such temperature sensors may be able to provide information particularly about tumors that are located near the surface of the prostate adjacent to the rectal wall.

Optionally, temperature sensors 110 can measure temperature accurately to within a precision of 1 degree Celsius, or 0.5 degrees, or 0.2 degrees, or 0.1 degrees, or 0.05 degrees, or 0.02 degrees, with an acquisition time less than 2 minutes, or less than 1 minute, or less than 30 seconds, or less than 10 seconds, or less than 3 seconds, or less than 1 second, or less than 0.3 seconds, or less than 0.1 second. Optionally, each temperature measurement is localized to within 1 centimeter, or 5 mm, or 2 mm, or 1 mm. Optionally, measurements are made at spatial intervals less than 1 cm, or less than 5 mm, or less than 2 mm, at least in the direction of the path of the needle, or in all directions within a volume of the prostate where the temperature is being measured by using needles that are spaced apart by such an interval.

Data interface 112 receives signals from temperature sensors 110, and optionally does some preliminary processing of the temperature data, for example converting the signals from analog to digital form, passing the data on to a controller 114, for example a personal computer, or specialized electronic circuitry. Ultrasound transducer 104 is connected to an interface 116, which optionally provides power to the transducer, and optionally provides preliminary processing of the ultrasound imaging data. Alternatively, power and preliminary processing for the ultrasound imaging are provided by different modules. Data on the ultrasound imaging is optionally passed on to controller 114, or a different controller, to produce images for display. The images are displayed on a monitor 118, or another display device, to guide the physician performing the biopsy. Optionally, monitor 118, or another display device, is also used to display temperature maps of the prostate, as will be described below.

Figure 1B:
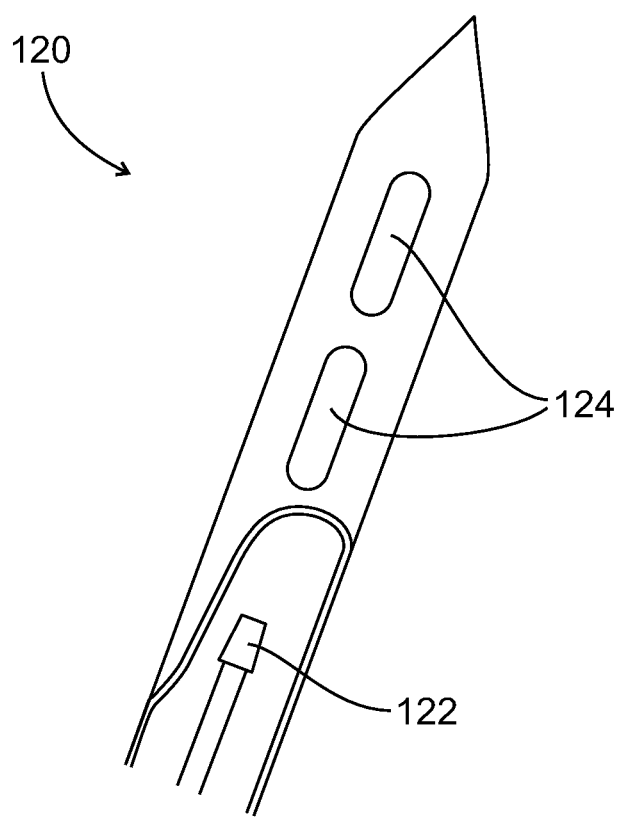
FIG. 1B schematically shows views of a needle that can be used instead of the needle shown in FIG. 1A, according to an exemplary embodiment of the invention.

FIG. 1B schematically shows a hollow needle 120, of a design that is optionally used instead of needle 108 in FIG. 1A. Needle 120, instead of or in addition to having one or more temperature sensors 110 mounted on the outside, has one or more temperature sensors 122 inside it, or built into a wall of the needle, and one or more temperature measuring locations 124 arranged along the side of the needle, and/or at its end. Optionally, one or more of the temperature measuring locations are open windows, or closed windows that are transparent to infrared, and the temperature sensor views the body tissue through the window, and measures the temperature of the tissue by infrared, for example, or the temperature sensor directly contacts the body tissue through the window and measures its temperature directly. The windows, for example, have a width between 10% and 30% of the needle diameter, or between 30% and 50%, or more than 50%, or less than 10% of the needle diameter. Optionally, the edges of the windows are smooth, at least on the outer surface of the needle, so they do not damage tissue. Optionally, instead of or in addition to having windows in the needle, one or more of the temperature measuring locations of the needle are solid regions of high thermal conductivity, and the surrounding structure of the needle is optionally made of a lower thermal conductivity material. The temperature sensors measure the temperature of each of these high thermal conductivity regions either by measuring infrared radiation from it, or by a direct contact temperature measurement, thus providing an indication of the temperature of the body tissue in contact with the high thermal conductivity region on the outside of the needle. In some embodiments of the invention, the temperature sensors are fixed in place, one for each temperature measuring location. In other embodiments of the invention, the temperature sensors are moveable, and can be withdrawn from the needle. For example, one or more temperature sensors are located in a channel in the needle that is used for taking a biopsy sample, and optionally sense the temperature through a window used for taking a biopsy sample, and are withdrawn from the channel before taking the biopsy sample, to make room for the biopsy sample. If the temperature sensor is moveable, then optionally there is only one temperature sensor which moves from one temperature measuring location to the next, measuring the temperature at each location sequentially, optionally after the needle has been inserted. Optionally, if the temperature sensor is moveable, it is not inserted into the needle until after the needle has been inserted into the prostate.

In some embodiments of the invention, needle 120 is first inserted into the prostate, all the way through the prostate, or a substantial part of the distance through the prostate, or deep enough to cover a portion of the prostate that is to be biopsied, for example a portion that is believed to be most likely to harbor cancer. Optionally, needle 120 is inserted using an intra-perineal procedure, so that it is oriented along the longest dimension of the prostate, which is typically 5 to 12 cm long. At this initial insertion, a biopsy sample is not taken, but a temperature profile is measured along the length of the needle, following ultrasound heating, using any of the methods described above for using needle 120. Optionally, this temperature profile is measured only after the needle has been inserted all the way. Alternatively, the temperature profile is measured sequentially at different locations as the needle is inserted, optionally pausing at each location to allow time for an accurate measurement. Because the needle is narrow, it is not expected to significantly affect the temperature profile itself, even if it is made of a good thermal conductor, and any such effect can be reduced by using a relatively low thermal conductivity material for the needle. Inserting the needle along the longest dimension of the prostate allows the temperature profile to be measured at a larger number of independent locations, and allows a temperature map covering most of the prostate to be made with fewer needle insertions, than if the needle were inserted along a shorter dimension of the prostate.

Once the temperature profile is known, a decision may be made, based on the temperature profile and optionally on other data as well, as to the temperature measuring locations 124 along the length of the needle where cancer is most likely to be located. The temperature sensor or sensors are optionally withdrawn from the needle, and a biopsy sample is taken from one or more of the temperature measuring locations where it is decided that cancer is most likely to be located. If the temperature measuring locations are open windows, then optionally the biopsy sample is taken through the window at that temperature measuring location. In some embodiments of the invention, the temperature measuring locations are closed areas with good thermal conductivity, but can be opened up in order to take biopsy samples through them, for example by rotating a sheath, on the inside or the outside of the needle, to uncover openings. Further details of how temperature is measured and a biopsy sample is taken, according to an exemplary embodiment of the invention, are provided below in the description of FIGS. 8 and 9.

Temperature Measurements

Figure 2:
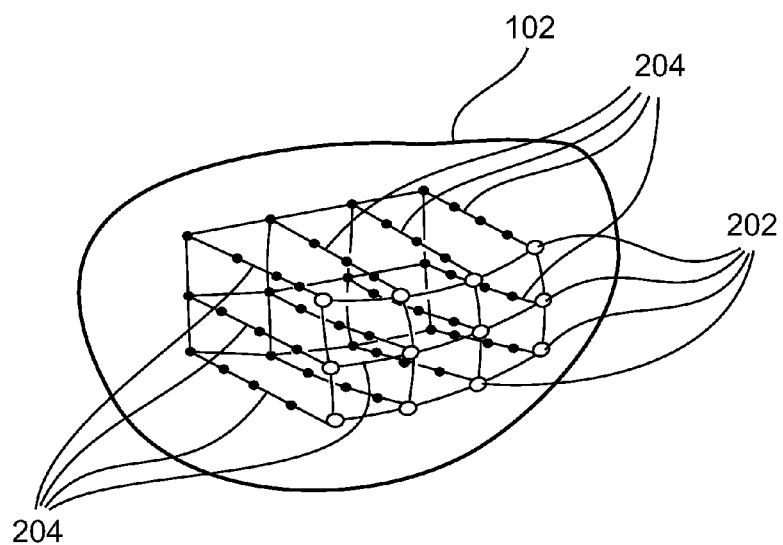
FIG. 2 is a schematic perspective view of a grid on which temperature is measured in the prostate, using the system of FIG. 1A.

In the prior art and in some embodiments of the invention, prostate biopsies are optionally taken from a plurality of locations distributed over the prostate, because it is not generally possible in advance to distinguish cancer from normal tissue. FIG. 2 shows an array of twelve target points 202 on the surface of prostate 102, each target point shown as a small circle. For each target point 202, a biopsy needle is inserted through the target point, along a path 204. A temperature measurement is made at each of a plurality of locations along each path 204, shown as a sequence of black dots in FIG. 2, using one of the methods described above. All of the points where temperature is measured comprise a grid which optionally covers most of the volume of prostate 102. Although the paths are shown schematically as being approximately parallel to each other in FIG. 2, they need not be approximately parallel. In general, the positions and orientation angles of the paths may be constrained by limited access to the prostate through a rectal biopsy probe.

Figure 3:
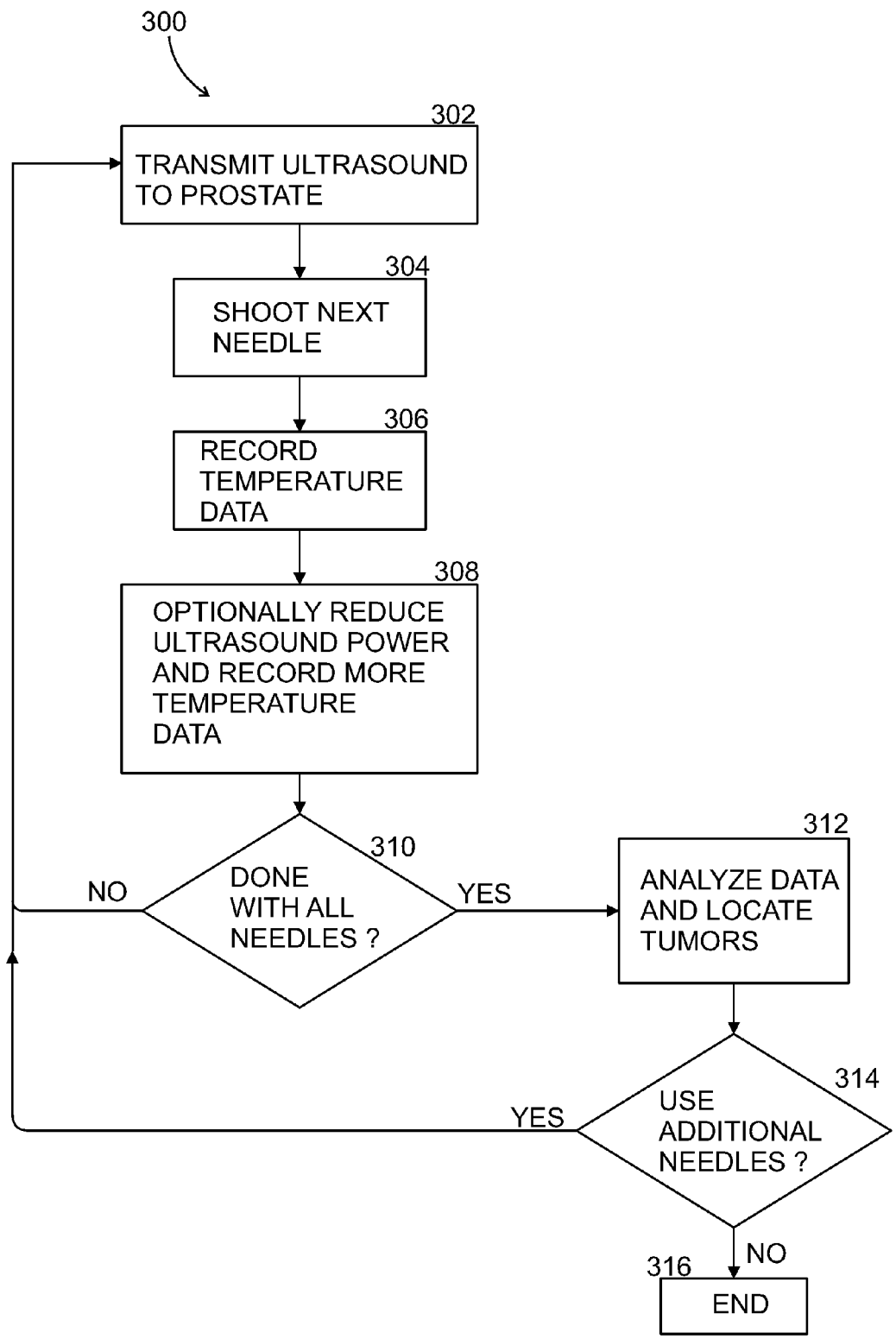
FIG. 3 is a flow diagram for a biopsy procedure of the prostate, using the system of FIG. 1A, according to an exemplary embodiment of the invention.

FIG. 3 shows a flow diagram 300 for using biopsy system 100. At 302, ultrasound is transmitted to the prostate. Optionally, the transmitted ultrasound is only the ultrasound used for imaging the prostate to guide the biopsy, as is done in prior art prostate biopsy systems. Such ultrasound is usually transmitted as a series of pulses, with pulse rates typically between 200 and 5000 pulses per second. Optionally, an existing off-the-shelf prostate biopsy ultrasound system is used for this purpose, in some embodiments with higher power than would normally be needed for imaging, in order to heat the prostate enough to measure temperature changes. Alternatively, an additional component of ultrasound is transmitted, optionally not pulsed, or pulsed at a much lower pulse rate, for example fewer than 100 pulses per second, or fewer than 50, fewer than 20, or fewer than 10 pulses per second, in addition to the ultrasound pulses used for imaging, in order to heat the prostate sufficiently. Each pulse of the additional component of ultrasound, or the entire transmission if it is not pulsed, lasts for at least 0.01 seconds, or at least 0.02 seconds, or at least 0.05 seconds, or at least 0.1 seconds, or at least 0.2 seconds. If the additional component is pulsed, it has a duty cycle of at least 1% or at least 2% or at least 5% or at least 10% or at least 20%.

The additional heating component can, but need not, have the same frequency, or range of frequencies, as the ultrasound used for imaging. In particular, it may be advantageous to use higher frequency ultrasound for imaging, for example 7 to 10 MHz, to get higher resolution images, and to use lower frequency ultrasound for heating, to get more uniform and deeper heating and/or to get greater sensitivity of heating rate to tissue type. The inventor has done in-vitro tests indicating that the absorption rate of ultrasound at 1 MHz distinguishes better between different tissues, in particular between chicken liver and beef liver, than the absorption rate of ultrasound at 3 MHz.

Ultrasound frequencies as low as 300 kHz or 500 kHz, or frequencies between 300 kHz and 1 MHz, or between 1 and 3 MHz, may also be used for heating. In some embodiments of the invention, higher frequency ultrasound, for example between 3 and 5 MHz, or between 5 and 15 MHz, are used for heating, particularly in cases where the ultrasound does not have to penetrate very far into the tissue. Using higher frequency ultrasound may have the potential advantage that it is less likely to cause cavitation in the tissue for a given heating power.

In some embodiments of the invention, a different imaging modality is used to guide the biopsy, such as magnetic resonance imaging or electric impedance imaging, and the ultrasound is used only for heating the prostate to measure the temperature changes. In some embodiments of the invention, even if ultrasound imaging is used to guide the biopsy, the ultrasound transmitted into the prostate initially, before performing the biopsy, is only used for heating the prostate, and is optionally not pulsed, or is pulsed at a much lower pulse rate than ultrasound used for imaging. However, the ultrasound used for heating may be pulsed rapidly, for example if the heating is done by an off-the-shelf ultrasound system that is designed for imaging.

In some embodiments of the invention, ultrasound is initially used only for imaging to guide the biopsy, or, if the biopsy needle is not guided by ultrasound imaging, then ultrasound is not transmitted at all initially. Only after the biopsy needle has been inserted, and one or more temperature measurements have been made to provide a baseline with little or no heating, is substantial ultrasound power transmitted to heat the prostate. Such a baseline measurement may allow a more accurate assessment of the absolute and relative degree of heating of the tissue at different locations, and may also reveal temperature differences between tumors and normal tissue that may exist independently of ultrasound heating, for example differences due to different metabolic rates or differences in blood circulation in healthy tissue and tumors.

Optionally, the ultrasound transducer is limited to transmitting a total ultrasound power per area transmitted into the prostate, the peak spatial time average power, of no more than 720 mW/$cm^2$, or no more than 430 mW/cm, which are limits imposed by the United States Food and Drug Administration for diagnostic ultrasound for different parts of the body. Optionally, the peak spatial time average power is less than 94 mW/$cm^2$, or less than 17 mW/$cm^2$. Optionally, these power limits apply to a time average over any time interval of at least 10 seconds, or at least 1 second, or at least 0.1 second. Optionally, the peak spatial pulse average power is less than 190 W/$cm^2$, or less than 28 W/$cm^2$. Optionally, the ultrasound transducer is prevented from exceeding at least one of these power limits, or an intermediate or more stringent power limit, by hardware, for example by a protection circuit which shuts off the transducer if this power limit is reached. Alternatively or additionally, software, for example in controller 114, prevents the power limit from being exceeded. In some embodiments of the invention, the system is physically capable of running at higher power, but is provided with a control knob, or with an input parameter that can be entered into controller 114 by a user, which limits the power, and one of these power limits is chosen, or recommended to the user, for example in order to meet FDA requirements.

Optionally, the prostate never increases in temperature by more than 1, 2, 3, or 4 degrees Celsius, or never exceeds 38, 39, 40, or 41 degrees Celsius, as a result of the ultrasound transmitted into it.

Optionally, the biopsy is not performed until the ultrasound has been heating the prostate for a long enough time so that the prostate has reached thermal equilibrium, with a balance between heating from the ultrasound, and cooling from blood circulation and from thermal conduction and other heat transport into surrounding tissues. For example, the heating is continued for more than 1 minute, or more than 3 minutes, or more than 5 minutes. A potential advantage of waiting until thermal equilibrium has been reached, is that the temperature profile measured during the biopsy will not be sensitive to exactly how long the heating has been going on before the biopsy is performed, and the temperature measured by different biopsy needles, at different times, can be meaningfully compared. Alternatively, the biopsy is performed before thermal equilibrium has been reached, or not necessarily waiting until thermal equilibrium has been reached, and thermal modeling is optionally used when evaluating the temperature measurements and comparing measurements from different biopsy needles taken at different times.

At 304, a biopsy needle is shot or otherwise advanced into the prostate. At 306, the temperature is recorded by one or more temperature sensors on the needle. Optionally, as described for FIG. 1, there is a plurality of temperature sensors arranged along the needle, and the temperature is measured simultaneously by the different sensors at different locations along the needle. Alternatively or additionally, the temperature is measured sequentially by each temperature sensor, or by a single temperature sensor, at different locations along the path of the needle, as the needle is withdrawn from the prostate, or as the needle is re-inserted after being partly withdrawn. Optionally, the needle is moved slowly enough, and/or its motion is paused each time the temperature is measured, so that accurate measurements can be made. Optionally, ultrasound power continues to be transmitted after the needle has been shot into the prostate, even if ultrasound imaging is no longer needed for guidance in placing the needle, such that the temperature remains at a constant value at each location, in thermal equilibrium, during the measurement, and between the measurements with this needle and the next needle. Alternatively, the ultrasound power is decreased, or shut off completely, after the needle is placed, and thermal modeling is optionally used when analyzing temperature data taken at different times.

In some embodiments of the invention, instead of using a biopsy needle to measure temperature, another needle, not necessarily hollow and not necessarily shot rapidly into the prostate, is inserted into the prostate and used to measure temperature. Alternatively or additionally, temperature is measured by sensors outside the prostate, adjacent to the rectal wall. One or more biopsy samples are only taken later, once the temperature of the prostate has been mapped. Optionally, temperature is also measured by the biopsy needles when the samples are taken. Optionally, biopsy samples are taken from only a limited number of paths, responsive to the locations of tumors as indicated by the temperature data.

Optionally, at 308, the temperature is measured again at one or more locations along the path of the needle, after reducing or shutting off the ultrasound power. As at 306, a plurality of temperature sensors located along the length of the needle may be used, or a single temperature sensor may be used, located optionally at the end of the needle, and the temperature may be measured simultaneously at different locations, and/or sequentially while withdrawing the needle. If the needle was withdrawn while making the temperature measurements at 306, then optionally it is not withdrawn completely, but the tip remains in the prostate, and it is optionally pushed back into the prostate along the same path, in order to perform the temperature measurements again, at 308. Making a second set of temperature measurements with the ultrasound power shut off or reduced provides a measure of the cooling rate of different locations in the prostate. Like the heating rate, the cooling rate may also differ between cancer and normal tissue, due for example to increased blood circulation in malignant tumors. Typical characteristic cooling times for normal tissue, raised in temperature by a few degrees Celsius, are several minutes. Optionally, additional measurements are made with the same needle at one or more later times, for example 30 seconds later, or one minute later, or 2 minutes later, when the temperature has decreased further, to provide additional information on the cooling rate. When all of the temperature measurements with that needle have been completed, the needle is completely withdrawn, and the biopsy sample is saved, optionally according to the normal procedure for prostate biopsies.

In some embodiments of the invention, in particular those embodiments where the prostate is not significantly heated before inserting the biopsy needle, the ultrasound power may be turned on or increased before measuring the temperature at 308, instead of being turned off or reduced. The temperature measurements made at 306 then provide a baseline temperature before substantial heating, and the temperature measurements at 308 provide a measure of the rise in temperature due to absorption of ultrasound. Optionally, the ultrasound power is then turned off or reduced, and temperature measurements are made at one or more additional time intervals later, to measure the cooling rate.

In some embodiments of the invention, temperature measurements are made first during or after heating the prostate with ultrasound at a first frequency. The prostate is then heated with ultrasound at a second frequency, and a second set of temperature measurements is made. If the prostate has not had time to cool completely from heating at the first frequency, then the residual heat from the first heating is optionally taken into account in analyzing the second set of temperature measurements. Measuring the effect of heating at two different ultrasound frequencies may provide additional information for identifying tumors, for example.

At 310, if all of the desired biopsy samples have not been taken yet, the flow diagram returns to 302, and ultrasound is optionally transmitted to heat the prostate, and/or to provide ultrasound imaging guidance, for the next biopsy needle. In some embodiments of the invention, the prostate is substantially heated before temperature measurements are made with the first needle, but not immediately before using one of more of the subsequent needles, and temperature measurements made with those needles rely on residual heat remaining in the prostate from the earlier ultrasound absorption.

Optionally, the different elapsed times since heating, for the different needles, are taken into account when analyzing the data, to provide maps of both energy absorption and cooling rate. Optionally, a first set of needles is used, widely distributed over the volume of the prostate, during heating or shortly after heating. A second set of needles, optionally interleaved with the first set and also widely distributed over the volume of the prostate, is used after the heating, at a time interval after the first set long enough for significant thermal transport to occur. Interpolating the temperature data from each set of needles allows temperature maps for the whole prostate to be calculated at two different times.

Typically, biopsy needles are used at about 12 locations, covering much of the volume of the prostate, during a prostate biopsy, in current practice. In some embodiments of the invention, biopsy needles are used at fewer than 12 locations, optionally spaced to cover much of the prostate, and biopsy needles are used at additional locations only if indicated by the temperature data as described below.

Analysis of Temperature Data

If all of the desired biopsy samples have been taken, then at 312, the temperature data is analyzed, and is used to identify and/or estimate the location of possible tumors. Such tumors may show up, for example, as local maxima or local minima in the temperature, on a three-dimensional grid of data such as that shown in FIG. 2. Optionally, the temperature data on the discrete grid points is interpolated to estimate the locations of tumors centered between the paths of different needles. It may be possible to do this, even for a tumor smaller in diameter than the distance between adjacent needle paths, and even if the tumor is located entirely between the needle paths, because, as heat is transported from or to the tumor by blood circulation, and/or by thermal conduction or transported in other ways, a region around each tumor may become hotter or cooler than the rest of the normal tissue.

Optionally, other data obtained by the ultrasound is used, in conjunction with the temperature data, in identifying or locating tumors. For example, Doppler ultrasound data may be used, or ultrasound imaging data may be used.

At 314, a decision is made whether or not to use additional biopsy needles, to obtain biopsy samples of one or more tumors that appear to be located between the paths of the needles already used, based on the analysis of the temperature data done at 312. Such additional biopsy needles, in addition to possibly obtaining tissue samples from such a tumor that was missed by the other biopsy needles, are also optionally used to measure the temperature along their path, and can confirm or refute the existence of such tumors, and more accurately measure their location if they do exist. If a decision is made to use one or more additional biopsy needles, then the position and angle or orientation of their paths is chosen, based on the existing temperature data, and the flow diagram returns to 302. Temperature data measured by the additional biopsy needles may lead to a more accurate estimate of the location of tumors, and further biopsy needles may then be used to obtain samples from them. If no more biopsy needles are to be used, then the procedure ends at 316.

Optionally, the temperature data is used by a pathologist when examining the biopsy samples, for example to direct particularly close examination at certain parts of the samples, and/or to provide additional information for characterizing the stage of development of any cancer that is found.

Brachytherapy System and Procedure

Figure 4:
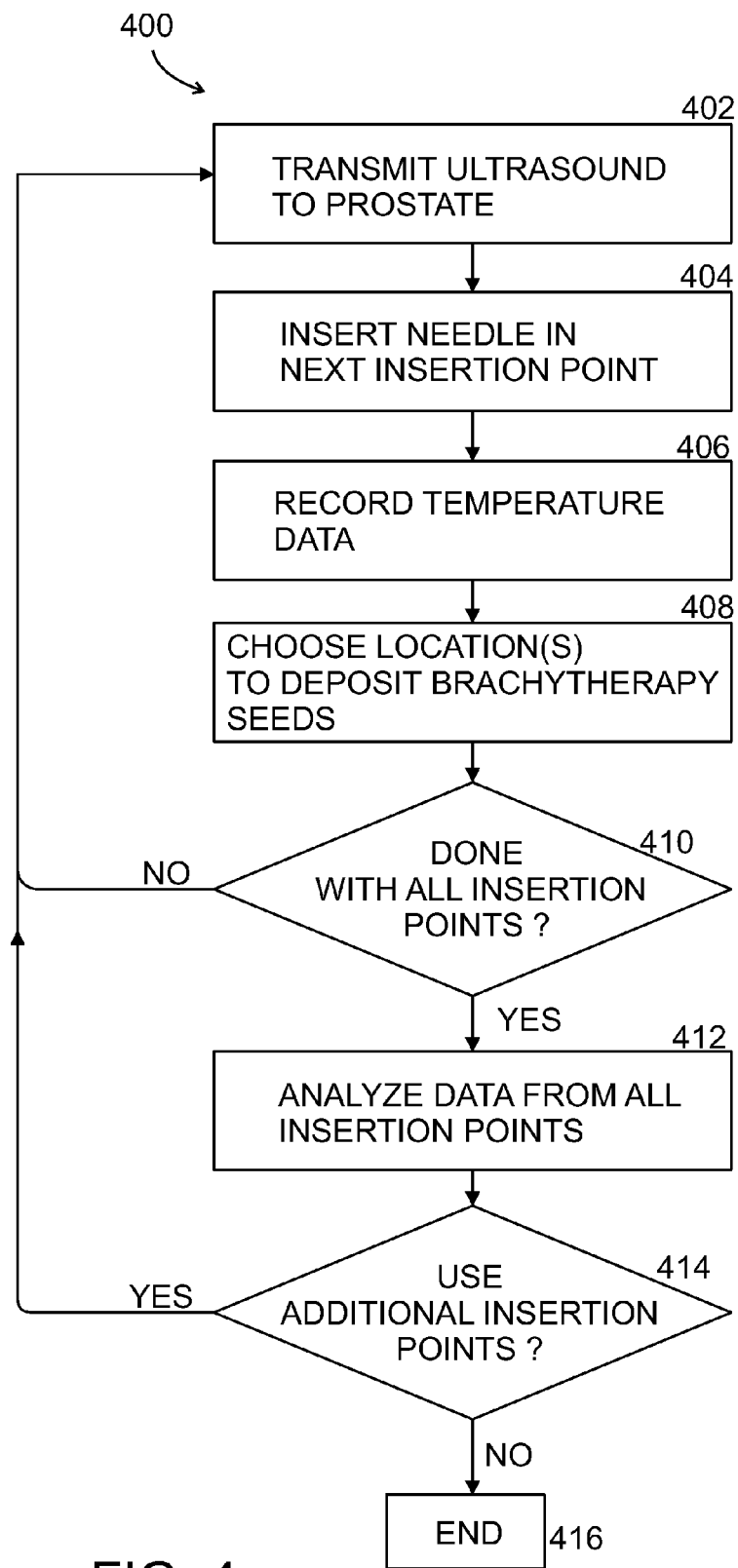
FIG. 4 is a flowchart for a brachytherapy procedure of the prostate, using the system of FIG. 1A, according to an exemplary embodiment of the invention.

FIG. 4 shows a flow diagram 400 for a brachytherapy procedure for treating prostate cancer, by depositing radioactive seeds at chosen locations in the prostate. The brachytherapy procedure is optionally performed using a brachytherapy system that could be illustrated by FIG. 1, but with biopsy needle 108 replaced by a brachytherapy needle, and with biopsy gun 106 replaced by an appropriate device for holding and inserting brachytherapy needles. The other elements of FIG. 1, including ultrasound transducer 104 and temperature sensors 110, could be used for the brachytherapy system as well as for the biopsy system. The needle paths 204 in FIG. 2, and the grid points at which temperature is measured, could also pertain to a brachytherapy system as well as to a biopsy system.

At 402, ultrasound is transmitted into the prostate. As in the case of flow diagram 300 in FIG. 3, the ultrasound is optionally only imaging ultrasound used to guide the placement of brachytherapy seeds, or may include a component specifically for heating the prostate to measure the temperature distribution. In general, the various options for the transmission of ultrasound described for FIG. 3 apply to FIG. 4 as well.

At 404, a needle containing one or more brachytherapy seeds is inserted into the prostate, at a planned needle insertion point on the surface of the prostate, for example one of points 202 in FIG. 2. Optionally, the needle insertion points are chosen to cover much of the volume of the prostate, and to be relatively uniformly spaced. This is typically done in brachytherapy of the prostate because it is generally not known where in the prostate tumors are located, so the brachytherapy seeds are placed in a relatively uniform way throughout the volume prostate, in order to destroy tumors that are found anywhere in the prostate, while trying not to harm healthy tissue in and near the prostate more than necessary. Alternatively, the locations of tumors are estimated, for example using temperature data measured during a previously performed biopsy, as described above for FIG. 3, and the insertion points for the brachytherapy needle are chosen so that seeds can be planted only close to these expected locations of tumors, or so that more seeds or seeds with more radioactivity are concentrated near the expected locations of tumors, providing them with a greater dose of radiation than the rest of the prostate.

At 406, temperature is optionally measured along the path of the needle. This is done, for example, using an array of temperature sensors arranged along the needle, optionally simultaneously. Alternatively, the temperature is measured sequentially at different locations along the path of the needle, optionally by a single temperature sensor, located for example near the tip of the needle, while the needle is being inserted, or being withdrawn. Any of the options for measuring the temperature described for FIG. 3 may be used, including the options for measuring the temperature while it is decreasing as described for 308. The temperature is optionally measured while the needle is being inserted initially, since a brachytherapy needle, unlike a biopsy needle, is generally not shot into the prostate with a gun. In some embodiments of the invention, temperature is not measured at all by the brachytherapy needle, but a temperature profile obtained previously, for example using the biopsy system as described for FIG. 3, is used as an approximation to the temperature profile along the path of the brachytherapy needle.

At 408, locations along the path of the brachytherapy needle are chosen to deposit radioactive brachytherapy seeds, using information about the locations of tumors derived from the temperature measurements. For example, seeds are planted only or primarily at or near locations along the path of the needle where the temperature has a local maximum, or where the temperature is higher than normal, since it is expected that more ultrasound power will be absorbed by malignant tumors than by healthy tissue. Limiting or concentrating the seeds to these locations has the potential advantage that the seeds may be more effective at killing cancer cells, and/or do less harm to healthy tissue, than if the seeds were distributed more uniformly.

Optionally, the temperature profile is measured over the entire path of the needle before depositing any seeds, even if that requires moving the needle back to a location that is has already passed in order to deposit the seeds. Alternatively, the seeds are deposited as the needle is inserted initially, deciding the locations of the seeds according to an algorithm that depends only on the local temperature, or only temperatures that the needle has already measured. Alternatively, the locations for depositing the seeds are decided based on a complete temperature profile, but previously acquired temperature measurements are used for the part of the path that the brachytherapy needle has not yet passed, or has not yet measured.

At 410, it is determined whether all of the planned needle insertion points have been used. If not, the flow diagram returns to 402 and 404, and the brachytherapy needle is inserted in the next needle insertion point. Optionally, for any needle insertion point, temperature data that has been obtained from the brachytherapy needle at previous needle insertion points is used in 408 when deciding where to plant the radioactive seeds for that insertion point.

Once all planned insertion points have been used, at 412 the temperature data is analyzed from all the insertion points, and optionally any previously obtained temperature data, for example from the biopsy procedure as described in FIG. 3, is used in the analysis as well. Using results of this analysis, which optionally includes estimates of the locations of malignant tumors in the prostate, as described for FIG. 3, a decision is made in at 414 whether to use any additional needle insertion points for the brachytherapy procedure. For example, if the analysis of the temperature data suggests that there is a tumor centered between the paths of the brachytherapy needle for two adjacent insertion points, then optionally an additional insertion point is used in order to deposit one or more radioactive seeds closer to the center of that tumor. If additional insertion points are to be used, then the flow diagram returns to 402 and 404, for the new insertion point. Optionally, additional temperature data is measured along the path of the needle for the new insertion point, in order to more precisely locate the center of the tumor before depositing the one or more additional seeds. If there are no more additional insertion points to be used, then the brachytherapy procedure ends at 416.

Breast Ultrasound System

Figure 5:
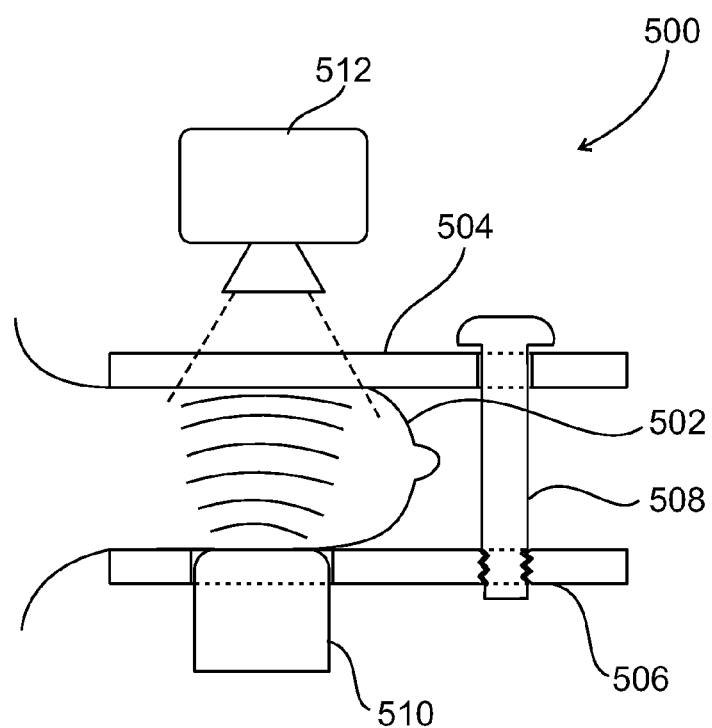
FIG. 5 is a schematic view of an ultrasound system for detecting breast cancer, according to an exemplary embodiment of the invention.
Figure 7:
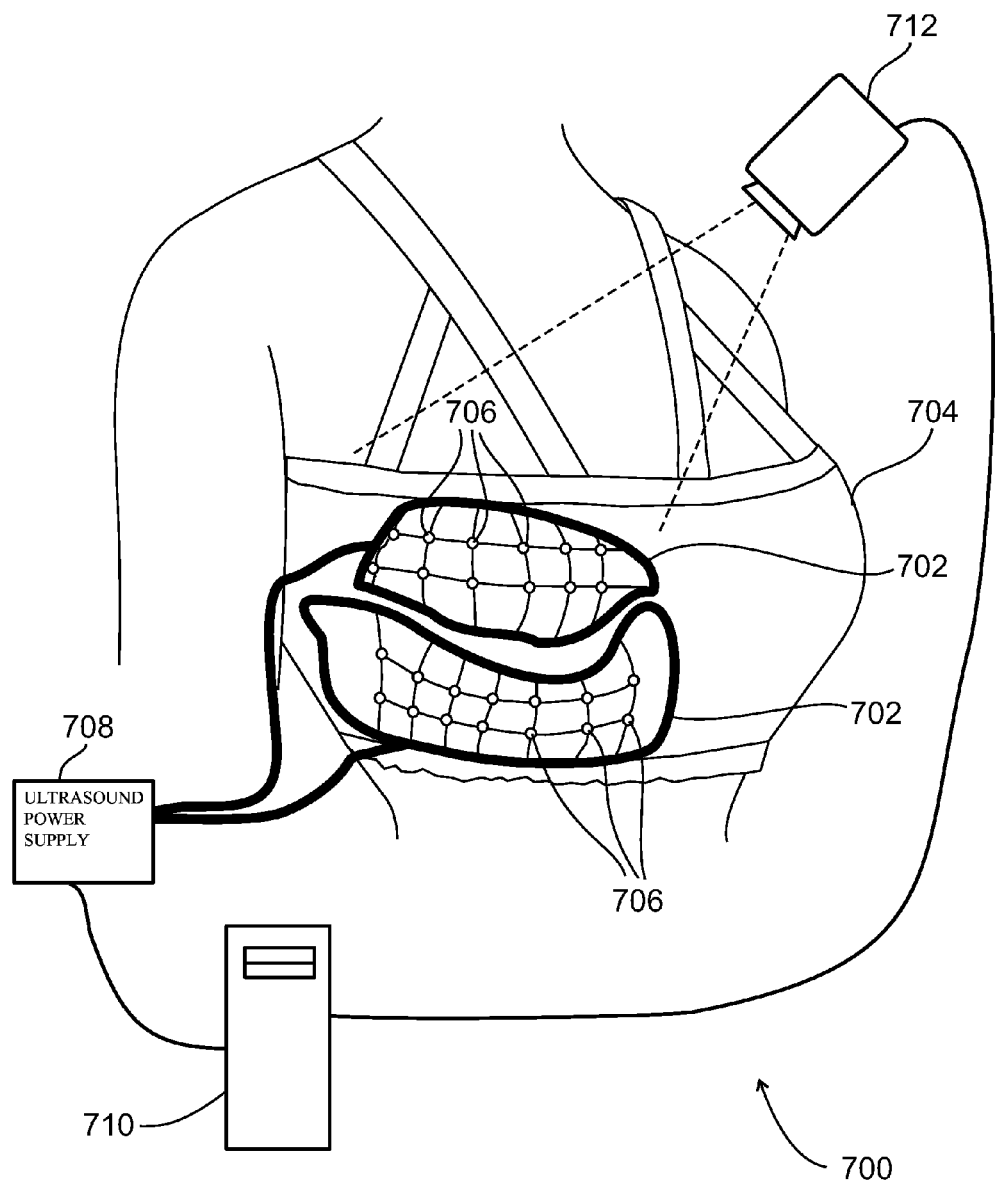
FIG. 7 a schematic view of an ultrasound system for detecting breast cancer, according to a different exemplary embodiment of the invention.

FIG. 5 schematically shows a system 500 for detecting and locating breast cancer, making use of the different thermal response of cancerous tissue and healthy tissue to ultrasound, and/or their different cooling rates. A similar system 700 with a somewhat different configuration is shown in FIG. 7, and described below. In system 500, a breast 502 is compressed, for example by being placed between plates 504 and 506. A tensioning element 508, for example one or more bolts, is optionally used to press the plates against opposite surfaces of the breast, flattening it. Optionally plates 504 and 506, and tensioning device 508, are constructed like the devices used to hold and flatten breasts in existing mammography or breast biopsy systems, or systems used for infrared mapping of breast temperature. An ultrasound transducer 510 transmits ultrasound waves into the breast, through an opening in plate 506, or directly through plate 506, heating the breast. Ultrasound transducer 510 is optionally configured to produce a relatively wide and uniform beam of ultrasound energy in a substantial part of the volume of the breast. Alternatively or additionally, transducer 510 scans the beam to distribute ultrasound power more uniformly in the breast, even if the beam is relatively narrow. The frequency of the ultrasound is optionally low enough, for example less than 2 MHz or less than 1 MHz, optionally as low as 500 kHz or even 300 kHz, so that the ultrasound power density is fairly uniform across the flattened breast, in the direction going from plate 506 to plate 504. Alternatively, higher frequencies are used, optionally up to 5 MHz, or even up to 15 MHz, especially if it is not desired to detect or locate cancer very deep in the breast. The power density of the ultrasound transducer, spatial peak time-averaged, is optionally limited to less than 720 mW/cm$^2$. The limit in power density may be imposed by hardware, by software, by a choice of value of a control parameter by a user, or by any combination of these, as described above for the prostate biopsy system in the description of FIG. 3. Optionally, any of the power limits described above for the prostate biopsy may apply here as well. Optionally, the breast never increases in temperature by more than 1, 2, 3, or 4 degrees Celsius, or never exceeds 38, 39, 40, or 41 degrees Celsius, as a result of the ultrasound transmitted into it.

In some embodiments of the invention, ultrasound transducer 510 transmits ultrasound waves into the breast, heating the tissue, before the breast is compressed. In this case, transducer 510 need not transmit ultrasound waves through plate 506, or through an opening in plate 506, but optionally ultrasound transducer is placed directly against the breast on an area that is not in contact with any plate, and the breast is compressed, for example between plates 504 and 506, only after the ultrasound power is applied. This has the potential advantage that the ultrasound absorption properties of the breast may be different when the breast is compressed, than when it is not compressed, and heating uncompressed breast tissue might better distinguish between healthy and cancerous tissue, for example. Compressing the breast before the temperature is measured, rather than also measuring the temperature on the uncompressed breast, has the potential advantage that localized regions of higher (or lower) temperature within the breast, such as breast tumors with different heating or cooling properties, may be brought closer to the surface, and be easier to detect and characterize. If a thermally significant time interval is allowed to elapse between heating the breast tissue and measuring the temperature, in order to allow the tissue to cool somewhat to reveal regions with different cooling rate, then compression of the breast may begin right after the heating, or after the cooling interval just before measuring the temperature, or at any time in between.

An infrared camera 512 images a surface of the breast through surface 504, which is optionally at least partially transparent to infrared, or has one or more openings through which the camera can detect the infrared. Infrared camera 512 works at wavelengths that are useful for measuring small changes in the surface temperature above body temperature, for example between 3 and 12 microns. Optionally, infrared camera 512 is, or is similar to, a commercially available infrared camera used for measuring body surface temperature, for example a FLIR brand, B-CAM Western-S model. Optionally, the temperature is accurately measured to within a precision of 1 degree Celsius, or 0.5 degrees, or 0.2 degrees, or 0.1 degrees, or 0.05 degrees, with a spatial resolution less than 1 centimeter, or less than 5 mm, or less than 2 mm, with an acquisition time less than 1 minute, or less than 30 seconds, or less than 10 seconds, or less than 3 seconds, or less than 1 second, or less than 0.3 seconds, or less than 0.1 second. Tumors may show up as local hot spots on the infrared image, during and shortly after the heating of the breast by the ultrasound, because they tend to absorb ultrasound more than normal breast tissue. Some types of tumors may show up as local cool spots, if they absorb less ultrasound than normal breast tissue. The tumors may also cool off faster than the other breast tissue, after the ultrasound power is removed, because they may have greater local blood flow than normal tissue.

Optionally, infrared images are made at more than one time during and following the ultrasound heating of the breast, in order to detect tumors by one or both of these effects. Optionally, at least one infrared image is also made before heating the breast, to provide a baseline temperature distribution. Such a measurement has the potential advantage that it could detect temperature differences between healthy and diseased tissue that exist even without heating the tissue, and may allow such temperature differences to be distinguished from temperature differences associated with different ultrasound absorption rates of tissue. For example, increased blood circulation in cancerous tissue may make cancerous tissue cooler, or increased metabolism may make cancerous tissue warmer, than surrounding normal tissue. Measuring both those effects, and differences due to different ultrasound absorption rates, may make it possible to more reliably distinguish diseased from healthy tissue. If the breast is not compressed during ultrasound heating, but is compressed only after the heating when the infrared images are made, then optionally the breast is also compressed to make infrared images before the ultrasound heating, which has the potential advantage that it may be easier to compare the images made before and after heating.

Optionally, infrared images are adjusted, for example by software, to take into account non-uniformity in the distribution of ultrasound in the breast.

Figure 6:
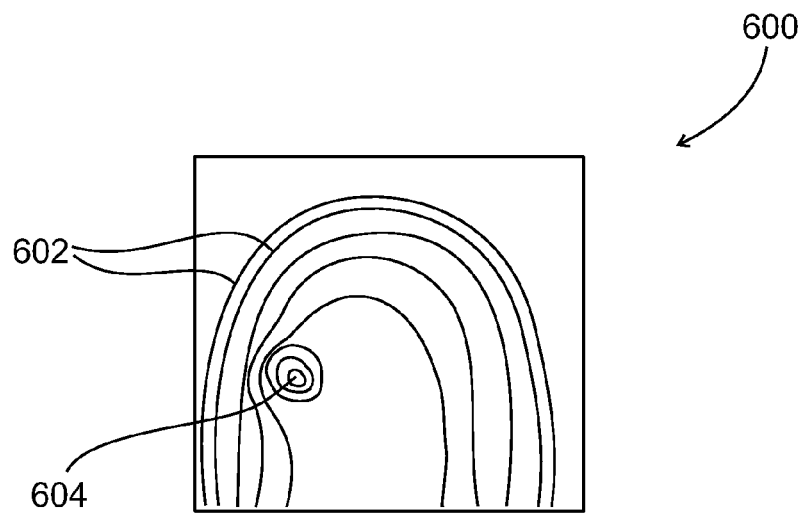
FIG. 6 is a schematic view of an infrared map of temperature of a breast, obtained using the system of FIG. 5.

Because breast 502 is relatively flattened by plates 504 and 506 and tensioning element 508, a two-dimensional infrared image of the surface of breast may reveal tumors with moderately high resolution. Typically, a tumor that is much smaller in diameter than the distance between the tumor and the surface of the breast might be expected to produce a local difference in temperature on the surface of the breast over a region with a diameter comparable to the depth of the tumor below the surface, which cannot be greater than the distance between plates 504 and 506. If that distance is relatively small compared to the dimensions of the breast, then the location of the tumor can be localized fairly well by the infrared camera. FIG. 6 shows an example of an infrared image 600, with contours 602 of constant surface temperature. A local peak 604 in temperature, or a local minimum in temperature, may indicate the location of a tumor.

The temperature is optionally determined from the infrared emission intensity at a given wavelength or range of wavelengths, and/or from an infrared spectrum, and/or from a peak emitted infrared wavelength. Optionally, the temperature is not calculated, but one of these parameters, or a combination of them, is used as a substitute for temperature, for locating tumors.

The infrared image may also be used to estimate the depth of the tumor below the surface of the breast. If higher frequency ultrasound is used, for example 3 MHz or higher, the ultrasound power may be mostly absorbed near the surface of the breast that is adjacent to ultrasound transducer 510. By comparing infrared images made using different ultrasound frequencies, an estimate can be made of the depth of the tumor. Comparing infrared images with ultrasound transducer 510 placed at different sides of the breast, for example by removing plates 504 and 506, exchanging their positions, and repositioning them around the breast, can also provide information about the depth of the tumor, because the diameter of the anomalous region may be different in the two images, depending on which side of the breast the tumor is closest to. Furthermore, if the ultrasound frequency is relatively high, then the ultrasound transducer will heat primarily one side of the breast in one image, and the other side of the breast in the other image.

Whether or not the infrared image or images are used to obtain information about the depth of the tumor, an infrared image such as image 600 is optionally used to guide a breast biopsy. A biopsy needle is inserted into the breast in region 604, for example. Optionally, one or more temperature sensors on the biopsy needle are used to measure the temperature of the breast as a function of the depth, during or following ultrasound heating the breast, similar to the temperature measurement by the prostate biopsy needle shown in FIG. 1. Knowing the temperature profile as a function of depth in the breast may allow the tumor to be located accurately in three dimensions, and a biopsy sample may then be taken of the tumor. Temperature data from the infrared camera, biopsy needle, or both, are optionally used by a pathologist to assist in making a diagnosis when examining the biopsy sample, as described above for prostate biopsies.

FIG. 7 schematically shows an alternative system 700 for detecting and locating breast cancer, also making use of the different thermal response of cancerous tissue and healthy tissue to ultrasound, and/or their different cooling rates. In system 700, the breast is not flattened between plates, but is surrounded by one or more flexible curved surfaces 702 held against the breast by a brassiere 704. A plurality of ultrasound actuators 706, for example piezo-electric actuators, transmit ultrasound into the breast. An ultrasound power supply 708, optionally controlled by a controller 710, for example a computer, supplies power to actuators 706. Optionally, the relative phases of the different actuators are set, for example by controller 710, in order to provide a relatively uniform distribution of ultrasound power to the breast. Optionally, such control is facilitated by having actuators 706 arranged in a regular array or pattern on curved surfaces 702. Optionally, there is a relatively large number of actuators that are spaced relatively close together, for example 10, 20, 50, or 100 actuators, or a smaller, larger, or intermediate number. Such an arrangement may allow a relatively large average ultrasound power density to be transmitted into the breast, without using too large a local power density, for example without ever exceeding 720 mW/cm$^2$. Optionally, actuators 706 are well coupled to the breast tissue by a gel or liquid between curved surfaces 702 and the breast, held in place by curved surfaces 702 and brassiere 704.

Ultrasound is transmitted into the breast for a period that is long enough to produce a measurable increase in temperature in the breast tissue at the power level used, for example for a period of 1, 2, 3, or 5 minutes, or for a longer, shorter, or intermediate period. A measurement of temperature as a function of position on the surface of the breast is then made, for example using an infrared camera 712. Infrared camera 712 may have any of the characteristics described above for infrared camera 512 in FIG. 5. Optionally, curved surfaces 702 and brassiere 704 are opened up, or removed from the breast, before the temperature measurement is made, allowing the surface of the breast to be viewed directly. Optionally, the temperature measurement is made within a short enough time after the ultrasound transmission stops, for example shorter than 1, 2 or 3 minutes, so that any differences in temperature due to different heating and/or cooling rates in different parts of the breast, for example in healthy and cancerous tissue, do not decrease very much due to heat transport within the breast. Optionally, a temperature measurement is also made before heating the breast tissue with ultrasound, to provide a baseline temperature distribution, as described above for FIG. 5.

One or more infrared images made by camera 712 are optionally used to locate a tumor in the breast, using any of the methods described above for system 500. Optionally, the one or more images are sent by camera 712 to controller 710, or to a different computer, which saves, processes, and/or analyzes the images.

Optionally, using either system 500 or system 700 or any similar system, software is used to process the image, for example by sharpening it. Sharpening may be done, for example, using commercially available software that is used to process images that are out of focus. Alternatively, software is used that is specifically designed and/or optimized to recover images that are blurred by diffusion, which generally has a different effect on images than blurring by defocusing, although both cause a loss of resolution. Such image processing may help in detecting breast tumors that might otherwise be missed, for example because they are located too far below the surface of the breast, or in more precisely determining where a detected tumor is located in the breast. Image processing, or image analysis, may also be used to more precisely estimate how far below the surface of the breast a detected tumor is located. Optionally, image processing software, applied to an infrared image of the surface of the breast, is used to locate one or more breast tumors inside the breast, by making the assumption that the tumors are small or point-like.

Although a system such as system 700, where the breast is not flattened, may be less sensitive to tumors that are located relatively deep within the breast than a system such as system 500, system 700 may still be satisfactory for purposes of screening for breast cancer, since breast tumors are often located relatively near the surface. Also, for screening purposes, it may not be important to precisely determine the location of a suspected tumor, initially.

Optionally, in either system 500 or system 700, a different non-invasive temperature measurement technique is used, in addition to or instead of measuring infrared emission from the surface of the breast using camera 512 or 712. Optionally, the temperature of the breast tissue is mapped using a method that allows a direct volumetric measurement of temperature, rather than only measuring the surface temperature using infrared emissions, and inferring the internal temperature. This has the potential advantage that it may allow a tumor to be located more precisely in three dimensions, including the depth below the surface of the breast. One or more of the following non-invasive volumetric temperature measurement techniques may be used:

1) near infrared spectroscopy
2) microwave radiometry
3) ultrasound thermometry, using the heating ultrasound or diagnostic ultrasound from a different source
4) magnetic resonance thermometry
5) electric impedance tomography The first four of these techniques are described in the references cited above, particularly the Ph.D. thesis of Hollis, and also, in the case of ultrasound thermometry, the talks by Straube et al, and Arthur et al, and the paper by Seip and Ebbini. Electric impedance tomography can be used to find temperature volumetrically, because the specific impedance, or resistivity, of body tissue, may depend on local temperature, at least at relatively low frequency of the electric current and voltage, for example well under 100 kHz. Electric impedance tomography may be used to measure temperature absolutely, if the temperature dependence of resistivity for the type of tissue being measured is calibrated in advance, or it may be used to detect changes in temperature, and to compare temperature changes at different locations, even if the temperature dependence of resistivity has not been calibrated in advance.

Any of these non-invasive volumetric temperature measurement techniques may be used as well for detecting tumors or abnormal tissue in other parts of the body, including being used in the prostate to supplement the temperature measurements made by invasive probes, as described above.

Biopsy Needle and Procedure

Figure 8:
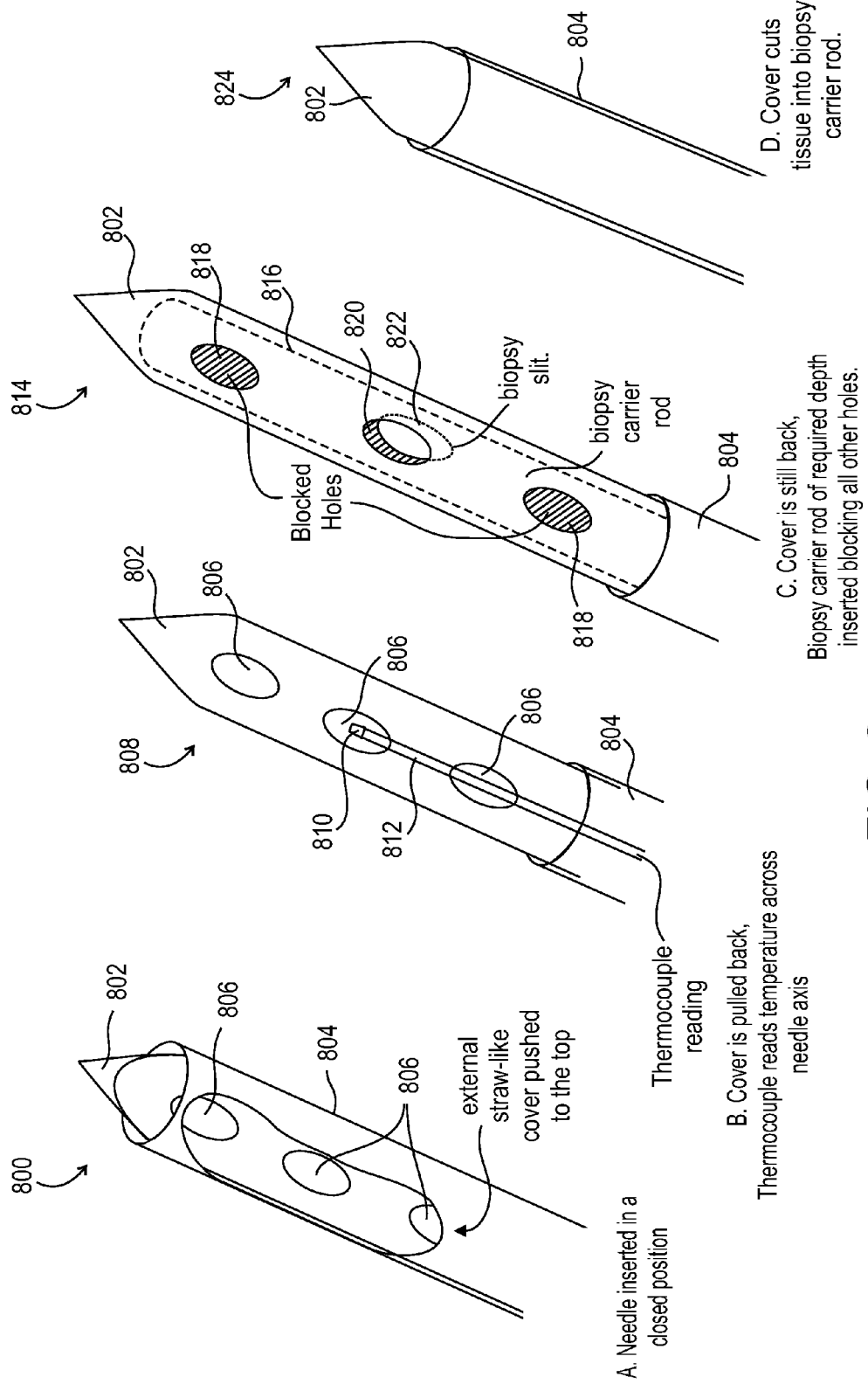
FIG. 8 shows a time sequence of schematic views of a biopsy needle during a biopsy procedure, according to an exemplary embodiment of the invention.
Figure 9:
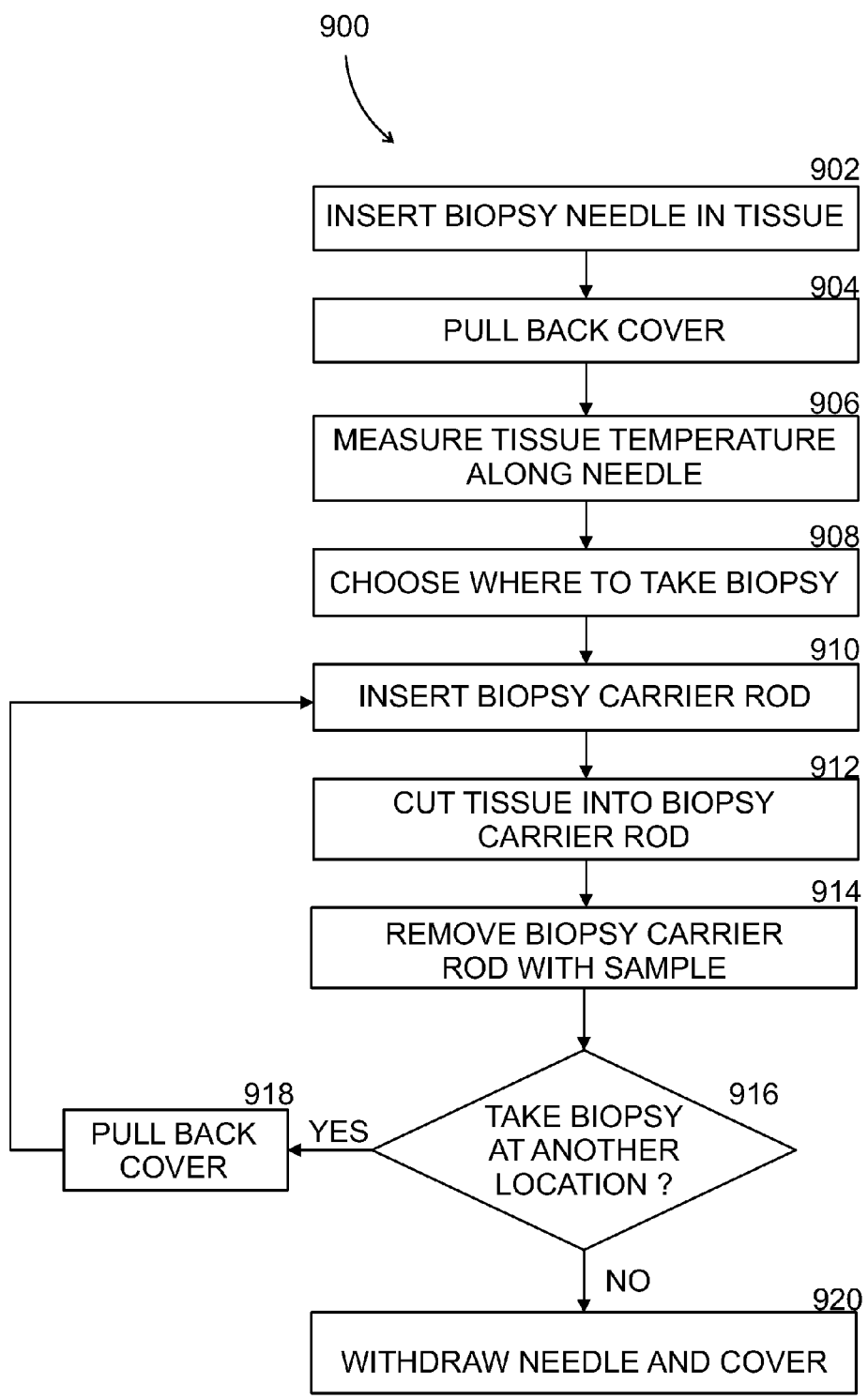
FIG. 9 is a flowchart for the biopsy procedure shown in FIG. 8, using the biopsy needle shown in FIG. 8.

FIG. 8 schematically shows a time sequence illustrating how a biopsy needle is used to take a biopsy sample, using temperature measurements to choose a location where the sample is taken, according to an exemplary embodiment of the invention. FIG. 9 is a flow chart 900 of the biopsy procedure. The first view in the time sequence, at the left of FIG. 8, shows a biopsy needle 800 when it is initially inserted into tissue, for example prostate tissue, at 902 in the flow chart. Needle 800 has a sharp point 802, and is initially in its closed position, pulled back into a cover 804, optionally with only point 802 outside the cover. A cutaway view shows the needle inside cover 804, with a plurality of windows 806 in the side of the needle, arranged along its length. Keeping the windows covered, while the needle is inserted, has the potential advantage of avoiding any damage to the tissue by sharp edges of the windows, and keeping tissue out of the inside of the needle until it has been decided exactly where to take a biopsy sample from. Optionally, the needle is pushed far enough into the tissue, at 902, so that it covers a full length of tissue over which the biopsy might be taken. For example, if it is used for a prostate biopsy, the needle is optionally pushed all or almost all of the way through the prostate.

Once the needle is in place, as shown in a next view 808 in the time sequence, cover 804 is pulled back, at 904 in the flow chart, exposing windows 806 to the surrounding tissue. A temperature sensor 810, for example a thermocouple, is then optionally pushed along the inside of the needle. At 906 in the flow chart, temperature sensor 810 makes temperature measurements of the tissue at each window 806. The temperature measurements are made after heating the tissue with ultrasound, in order to distinguish different types of tissue, for example healthy and cancerous tissue, by their different heating and/or cooling rates. Optionally, the temperature measurements are made sequentially, moving sensor 810 from one window 806 to another, along the needle axially. Optionally, some windows are also located at different azimuthal positions, and sensor 810 is moved azimuthally as well as axially from one window to another. Alternatively or additionally, temperature sensor 810 comprises a plurality of sub-sensors, which simultaneously measure temperature through different windows 806 in the needle. If all temperature measurements are made simultaneously, then there may be no need to move temperature sensor 810 in order to make the measurements, and optionally temperature sensor 810 is already in place when the needle is initially inserted into the tissue. One or more wires 812 optionally communicate temperature data to a data link located outside the body. Once the temperature measurement is made, temperature sensor 810 is optionally withdrawn from the needle. In some embodiments of the invention, the temperature sensor remains permanently in place in the needle. However, removing the temperature sensor may have the potential advantage that the temperature sensor will not interfere with taking the biopsy sample.

At 908 in the flow chart, a decision is made as to where along the needle to take a biopsy sample, based on the temperature measurements. Optionally, a location is chosen where cancerous tissue is more likely to be found, based on the temperature measurements. For example, if it is expected that cancerous tissue will have a higher temperature than healthy tissue as a result of ultrasound heating, and if the tissue was exposed to a fairly uniform power density of ultrasound along the path of the needle, then the biopsy sample may be taken at a window 806 where there is a local peak in the measured temperature. If the cancerous tissue is expected to have a lower temperature than healthy tissue, then the biopsy sample may be taken at a window 806 where there is a local minimum in measured temperature.

At 910 in the flow chart, as shown in view 814 of the time sequence, a biopsy carrier rod 816 is pushed along the inside of the needle. Carrier rod 816 is optionally closed on its side, with solid areas 818 blocking off windows 806 from the tissue, except for a biopsy slit 822, which is positioned adjacent to a window 820, one of the windows 806, where the biopsy sample is to be taken. When biopsy slit is positioned adjacent to window 820, then the inside of carrier rod 816 is exposed to tissue at that location. Optionally, different carrier rods are available, each with a biopsy slit at a different location, relative to the end of the carrier rod. Once a location has been chosen for the biopsy sample to be taken, one of the carrier rods is chosen, such that when the carrier rod is pushed all the way into the needle as far as it goes, the biopsy slit will be positioned at the right location for taking the biopsy sample, adjacent to window 820. Alternatively, the biopsy slit is always located near the end of the carrier rod, and the carrier rod is pushed into the needle only far enough so that the biopsy slit will be positioned adjacent to chosen window 820. Optionally, in this case, the carrier rod comprises a stopping element, which is adjusted before inserting the carrier rod, so that the carrier rod cannot be pushed too far into the needle.

At 912 in the flow chart, a tissue sample is cut off into the carrier rod, or into a pocket in the carrier rod located just inside the window. This is done, for example, by pushing cover 804 forward over the needle, as shown in view 824 of the time sequence. Before this is done, part of the tissue bulges through window 820 and biopsy slit 822 into the interior of carrier rod 816, due to the pressure of the tissue which has been pushed out of the way by the needle. Cover 804 has a sufficiently sharp edge, and/or there is a sufficiently tight fit between the needle and the cover, such that when cover 804 is pushed over the needle, the part of the tissue bulging into the interior of carrier rod 816 is cut off into the carrier rod. At 914 in the flow chart, the carrier rod is removed from the needle with the biopsy sample. Optionally, the needle and cover remain in place in the tissue when the carrier rod is removed.

At 916 in the flow chart, a decision is optionally made as whether another biopsy should be taken, at a different location along the needle. This decision is optionally based on the temperature profile of the tissue along the needle, measured at 906. For example, if the temperature profile suggests the presence of two separate tumors, indicated for example by two local maxima in temperature, then a choice might be made to take a biopsy sample from each of them. A choice might also be made to take two or more biopsy samples if it is difficult to tell, from the temperature profile, which location is most likely to have cancerous tissue. Optionally, the decision as to where all the biopsy samples will be taken is made after the temperature is measured, before any of the samples are taken.

If another sample is to be taken, then the cover is optionally pulled back again at 918. Alternatively, the cover is pulled back before the carrier rod is removed. However, keeping the cover closed while the carrier rod is removed may prevent tissue at other locations from entering any of windows 806 and interfering with the carrier rod, and/or from entering the carrier rod through the biopsy slit. Once the cover is pulled back, a new carrier rod is inserted at 910, and positioned to take the new biopsy sample, as described above for the first biopsy sample. Optionally, the cover is not pulled back until after the new carrier rod is inserted.

When all biopsy samples have been taken, the needle and cover are removed from the tissue at 920.

Figure 10:
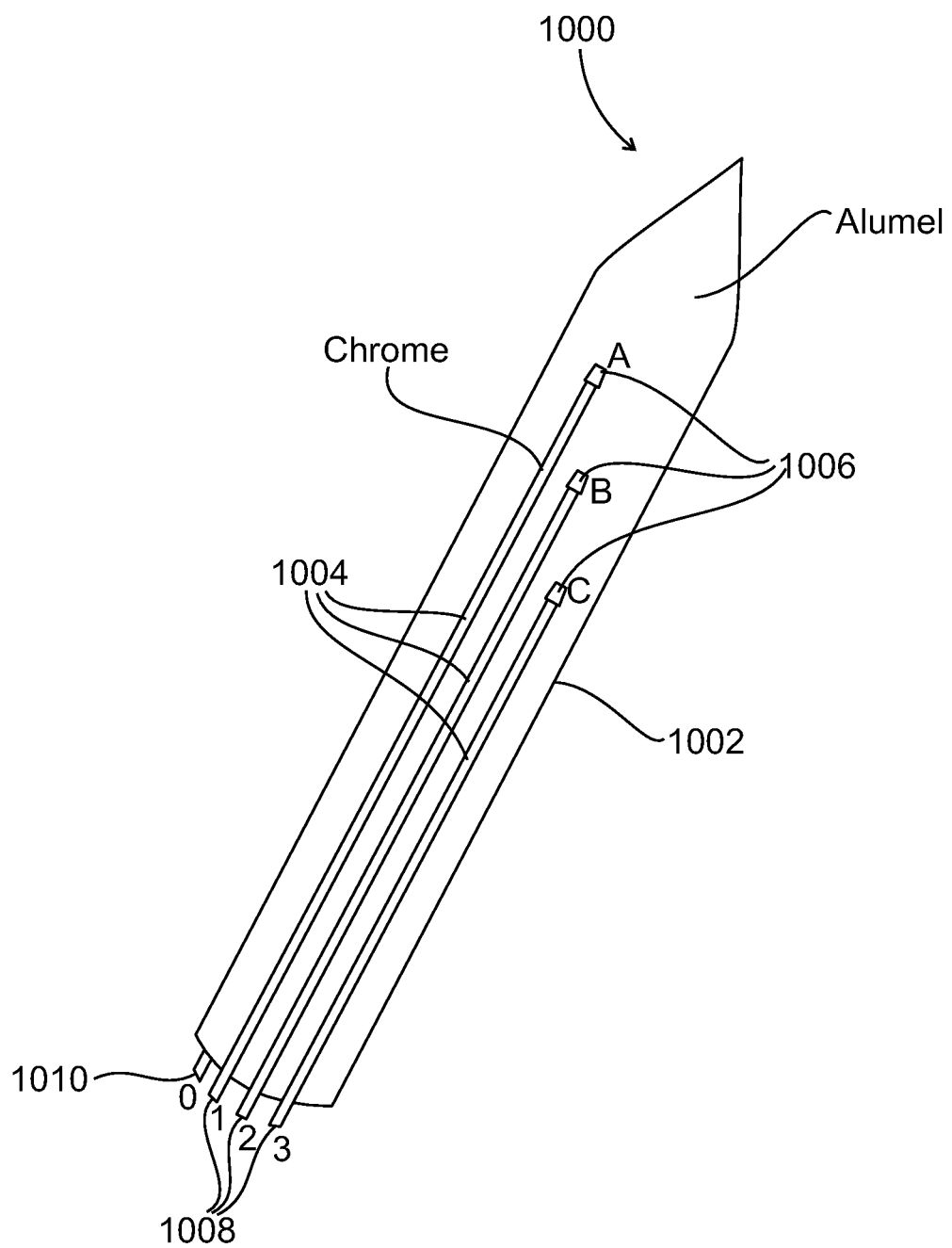
FIG. 10 is a schematic view of a biopsy needle with built-in thermocouples incorporating the wall of the needle, according to an exemplary embodiment of the invention.

FIG. 10 schematically shows a biopsy needle 1000 with built-in thermocouples, which may be used, for example, as an alternative to biopsy needle 800 in FIG. 8. A wall 1002 of needle 1000 is composed of one metal which may be used in thermocouples, for example alumel. One or more strips 1004, running along wall 1002 but electrically isolated from wall 1002, are made of a different metal which may be used in a thermocouple with the first metal, for example chromel. For example, strips 1004 are attached to wall 1002 with an electrically insulating glue. Each strip 1004 has a distal end 1006, where it is in good electrical contact with wall 1002, and where it is in good thermal contact with tissue adjacent to needle 1000 at that location. At the proximal end of each strip is an electrical lead 1008, and there is also an electrical lead 1010 electrically connected to the proximal end of wall 1002. Leads 1008 and lead 1010 are optionally kept at a constant, known temperature. Wall 1002, and each strip 1004, forms a thermocouple, with a potential difference between lead 1008 for that strip, and lead 1010, which depends on the temperature of distal end 1006 for that strip. Optionally, needle 1000 comprises a plurality of such strips, each with distal end 1006 at a different location along needle 1000. A temperature profile of the tissue along the length of needle 1000, relative to the known fixed temperature of leads 1008 and lead 1010, may then be determined by measuring the potential at each lead 1008, relative to the potential at lead 1010.

It should be noted that some features of needle 800 may be used in needle 1000, for example windows 806, optionally on a different side of the needle from strips 1004, cover 804, and carrier rod 816. Strips 1004 are optionally glued firmly in place along the inside or outside of wall 1002, and optionally are radially thin. This has the potential advantage that strips 1004 will not interfere with, or be damaged by, the sliding of any element along the outside of the needle, for example a cover, or the sliding of any element along the inside of the needle, for example a carrier rod.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate some embodiments of the invention in a non limiting fashion.

To demonstrate the feasibility of using different ultrasound heating rates to distinguish between otherwise similar types of tissue, in vitro tests were done in which a small piece of chicken liver was embedded in the surface of a larger piece of beef liver, or a small piece of beef liver was embedded in the surface of a larger piece of chicken liver. The entire sample was then heated uniformly by ultrasound at either 1 MHz or 3 MHz, at a time-averaged intensity lower than 720 mW/cm$^2$, for a long enough duration, which ranged from about 1 minute to about 6 minutes, so that its temperature rose by a few degrees Celsius. An infrared camera was used to image the surface of the sample, and to measure the temperature of the two types of liver. In all cases, it was found that the beef liver heated substantially faster than the chicken liver, and the two types of liver were easily distinguishable in the infrared image.

Table 1 lists data for the five tests that were done. In all tests, a therapeutic ultrasound machine, a Mettler Electronics Sonicator 740, was used, with a single transducer operating at 10% duty cycle. The machine was placed in a fixture with the transducer pointing upward, and set to generate a uniform unfocused beam of ultrasound. The sample was placed on top of the transducer. The temperatures before and after heating were measured using a FLIR brand, B-CAM Western-S model infrared camera. The initial temperature was between 20 and 25 degrees Celsius, with no detectable difference between the two types of liver. In tests 2 through 5, a gel was used to improve coupling between the transducer and the sample. The gel was not used in test 1, and a result, the coupling was inefficient, and a much longer heating time was used, over 6 minutes. This heating time was long enough to allow substantial conductive heat flux between the two types of liver, and as a result, the temperature rise in the two types of liver was much closer in test 1, than in the other tests. The chicken liver was embedded in the beef liver in tests 1 and 5, and the beef liver was embedded in the chicken liver in tests 2, 3, and 4.

TABLE 1

| | | | | | | |
|---|---|---|---|---|---|---|
| | | | Test Results | | | |
| Test # | Frequency | Average power, mW/cm$^2$ | Duration of heating, seconds | Temperature rise of beef liver | Temperature rise of chicken liver | Ratio of heating rates |
| 1 | 1 MHz | 220 | 387 | 5.9° C. | 4.5° C. | 1.31 |
| 2 | 1 MHz | 220 | 95 | 1.9° C. | 0.7° C. | 2.71 |
| 3 | 3 MHz | 220 | 48 | 3.4° C. | 1.9° C. | 1.81 |
| 4 | 3 MHz | 220 | 47 | 3.2° C. | 1.6° C. | 2.00 |
| 5 | 3 MHz | 160 | 147 | 2.6° C. | 0.9° C. | 2.89 |

The results show that the heating rates are higher for 3 MHz ultrasound than for 1 MHz ultrasound. Ignoring test 1 in which the chicken liver was significantly heated conductively by the surrounding beef liver, the data marginally suggest that the 1 MHz ultrasound may better distinguish between the two types of tissue than the 3 MHz ultrasound. For clinical use, the deeper penetration of the 1 MHz ultrasound in tissue, because it is not absorbed as much as the 3 MHz ultrasound, may also be advantageous. Comparison of tests 3, 4, and 5 shows that, within the precision of the temperature measurements, the heating rates of the two types of liver are repeatable, and proportional to the ultrasound power, as expected.

A test was also done with a chicken leg, applying the transducer from the back of the leg, at 1 MHz, with 700 mW/cm$^2$ average power. An infrared image taken after the heating showed greater ultrasound absorption by tendon tissue than by the surrounding muscle tissue.

An in vivo test was done to demonstrate that ultrasound heating can be used to distinguish necrotic from normal liver tissue in a rat, and that image processing is useful for this purpose. An ultrasound transducer of 10 cm$^2$ area was applied to the liver, with 1.4 W/cm$^2$ of ultrasound at 1 MHz, for a duration of 4 minutes. An infrared image, processed using standard Photoshop image sharpening software, clearly distinguishes the necrotic tissue from the normal tissue after the ultrasound heating, even though most of the necrotic tissue was several millimeters below the surface of the liver, and it is not as well distinguished from the normal tissue in the unprocessed infrared image. In the processed infrared image, the necrotic tissue had an infrared temperature of 28° C., while the normal liver tissue had an infrared temperature of 29° C., reflecting the lower rate of ultrasound heating in the necrotic tissue than in the normal tissue.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for characterizing a region of tissue in a body, comprising:
   a) transmitting a relatively uniform beam of ultrasound from a transducer at least 3 cm across into the body to the region of tissue, with a spatial peak power level, time-averaged over any one second interval, of less than 720 mW/cm$^2$, heating the body tissue by less than 3 degrees Celsius;
   b) measuring temperature of the tissue, at a plurality of locations, or at a plurality of times, or at a plurality of locations and at a plurality of times, during the ultrasound transmission, following the ultrasound transmission, or both; and
   c) using the temperature measurement to determine at least one property of the body tissue, based on differences in absorption of ultrasound, differences in cooling rate of the tissue following the ultrasound transmission, or both.

2. A method according to claim 1, wherein determining at least one property of the body tissue comprises finding cancerous tissue and distinguishing it from normal tissue.

3. A method according to claim 2, also including placing at least one brachytherapy seed at a location responsive to a location of the cancerous tissue.

4. A method according to claim 2, wherein the cancerous tissue is distinguished by its greater heating rate by the ultrasound that heats the body tissue.

5. A method according to claim 2, wherein the cancerous tissue is distinguished by its more rapid cooling rate following the transmission of the ultrasound.

6. A method according to claim 2, also including placing an invasive probe in the tissue, wherein measuring the temperature is done along a path of the probe.

7. A method according to claim 6, wherein the invasive probe comprises a biopsy needle or a needle for implanting brachytherapy seeds.

8. A method according to claim 7, wherein the invasive probe comprises a biopsy needle, wherein measuring the temperature is done by a moveable temperature sensor located inside the needle, also including removing the temperature sensor from the needle after measuring the temperature, to make room for a biopsy sample.

9. A method according to claim 7, also including taking a biopsy sample with the needle, after measuring the temperature, at a location chosen in response to a location of the cancerous tissue as determined from said temperature measurement.

10. A method according to claim 6, also including placing a biopsy needle in the tissue along a different path responsive to a location of the cancerous tissue, and taking a biopsy sample with the biopsy needle along the different path.

11. A method according to claim 6, wherein the temperature is measured at a plurality of locations while the probe is in place, or sequentially as the probe is moved.

12. A method according to claim 6, wherein the tissue comprises prostate tissue.

13. A method according to claim 6, wherein the temperature is measured sequentially at a plurality of locations along the path of the probe, by a same temperature sensor associated with the probe, as the temperature sensor moves to each of the locations.

14. A method according to claim 13, wherein the temperature sensor is fixed to the probe, and moves to the locations when the probe moves along the path.

15. A method according to claim 13, wherein the probe comprises a hollow needle with a channel inside, and the temperature sensor moves to the locations by moving along the channel inside the needle.

16. A method according to claim 1, wherein measuring the temperature comprises measuring an emitted infrared distribution on an outer surface of the body.

17. A method according to claim 16, wherein transmitting ultrasound comprises transmitting ultrasound at two different times, at two different frequencies that have different penetration depths in the tissue, measuring the temperature comprises measuring the emitted infrared distribution due to heating at each of the frequencies, and determining at least one property of the body tissue comprises determining dependence of the property on depth into the tissue.

18. A method according to claim 16, wherein the tissue is breast tissue, and characterizing body tissue comprises locating breast cancer.

19. A method according to claim 16, wherein using the temperature measurement comprises using image processing software to sharpen the measured infrared distribution.

20. A method according to claim 1, wherein measuring temperature of the tissue comprises using one or more of near infrared spectroscopy, microwave radiometry, ultrasound thermometry, magnetic resonance thermometry, and electric impedance tomography.

21. A method according to claim 1, wherein transmitting the ultrasound is done continuously for an interval of at least 0.1 seconds.

22. A method according to claim 1, wherein the ultrasound is transmitted into the tissue with power distributed relatively uniformly over most of the volume of an organ, and measuring the temperature comprises measuring a temperature resulting from the relatively uniform distribution of transmitted ultrasound.

23. A method according to claim 1, wherein the ultrasound is transmitted into the tissue for one minute or longer.

24. A system for characterizing a region of tissue in a body, comprising:
   a) an ultrasound transmitting system comprising a transducer at least 3 cm across, configured for transmitting a relatively uniform beam of ultrasound waves into the body to the region of tissue, limited to transmitting no more than 720 mW/cm² spatial peak power time-averaged over any one second interval;

b) a temperature measuring system that measures temperature of body tissue; and c) a controller that controls the ultrasound transmitting system to transmit the ultrasound waves into the body to the region of tissue, at a power and for a duration that will raise the temperature of the region of tissue by no more than 4 degrees Celsius, and that controls the temperature measuring system to measure temperature of the body tissue at one or more locations in the region of tissue, during the transmission of the ultrasound waves into the body, following the transmission of the ultrasound waves into the body, or both, thereby providing information for characterizing the tissue.

25. A system according to claim 24, wherein the temperature measuring system comprises an infrared camera for measuring temperature on an outside surface of the body.

26. A system according to claim 25, also comprising a compressing element for compressing a breast, wherein the infrared camera is positioned for making a map of temperature over a surface of the compressed breast.

27. A system according to claim 26, wherein the ultrasound transmitter is positioned for transmitting the ultrasound waves through the compressed breast over an extended area.

28. A system according to claim 24, also including a biopsy needle or a needle for implanting brachytherapy seeds, wherein the temperature measuring system comprises at least one temperature sensor associated with the needle.

29. A system according to claim 28, wherein the at least one temperature sensor comprises a plurality of temperature sensors arranged along the needle.

30. A system according to claim 28, wherein the at least one temperature sensor comprises a temperature sensor located inside the needle.

31. A system according to claim 24, wherein the temperature measuring system is capable of measuring temperature with a precision of better than 0.5 degrees Celsius, with a spatial resolution of better than 1 cm, in an acquisition time of less than one minute.

32. A system according to claim 24, wherein the controller determines at least one property of the body tissue using the temperature measurements.

33. A system according to claim 32, wherein the controller takes into account a relative timing of the ultrasound transmitting and the temperature measuring in determining the property of the body tissue.

34. A system according to claim 24, wherein the controller is configured to control the ultrasound transmitting system to transmit the ultrasound waves into the body for one minute or longer.

* * * * *